(12) United States Patent
Liu et al.

(10) Patent No.: US 10,709,130 B2
(45) Date of Patent: Jul. 14, 2020

(54) CLICKABLE ANTIMICROBIAL MOLECULES AND POLYMERS

(71) Applicant: ALEO BME, INC., State College, PA (US)

(72) Inventors: Chao Liu, State College, PA (US); Jianqing Hu, Guangzhou (CN); Kaimei Peng, Guangzhou (CN); Wei Ding, Guangzhou (CN)

(73) Assignee: ALEO BME, Inc., State College, PA (US)

( * ) Notice: Subject to any disclaimer, the term of this patent is extended or adjusted under 35 U.S.C. 154(b) by 144 days.

(21) Appl. No.: 15/823,775

(22) Filed: Nov. 28, 2017

(65) Prior Publication Data

US 2018/0146665 A1    May 31, 2018

Related U.S. Application Data

(60) Provisional application No. 62/426,668, filed on Nov. 28, 2016.

(51) Int. Cl.

| | | |
|---|---|---|
| *C07C 279/04* | (2006.01) |
| *A01N 47/44* | (2006.01) |
| *C07C 215/12* | (2006.01) |
| *A01N 33/12* | (2006.01) |
| *C08G 18/73* | (2006.01) |
| *C08G 18/38* | (2006.01) |
| *C08G 18/08* | (2006.01) |
| *C08G 18/10* | (2006.01) |
| *C08G 18/75* | (2006.01) |
| *C08G 18/48* | (2006.01) |
| *C08G 18/83* | (2006.01) |
| *C08L 75/14* | (2006.01) |
| *C08G 18/32* | (2006.01) |
| *C07C 215/24* | (2006.01) |
| *C08G 18/67* | (2006.01) |
| *G01R 33/46* | (2006.01) |
| *G01N 21/35* | (2014.01) |
| *A01N 33/08* | (2006.01) |

(52) U.S. Cl.
CPC ............ *A01N 33/08* (2013.01); *A01N 33/12* (2013.01); *A01N 47/44* (2013.01); *C07C 215/12* (2013.01); *C07C 215/24* (2013.01); *C07C 279/04* (2013.01); *C08G 18/0814* (2013.01); *C08G 18/10* (2013.01); *C08G 18/3275* (2013.01); *C08G 18/3819* (2013.01); *C08G 18/4825* (2013.01); *C08G 18/679* (2013.01); *C08G 18/73* (2013.01); *C08G 18/755* (2013.01); *C08G 18/833* (2013.01); *C08L 75/14* (2013.01); *G01N 2021/3595* (2013.01); *G01R 33/46* (2013.01)

(58) Field of Classification Search
None
See application file for complete search history.

(56) References Cited

U.S. PATENT DOCUMENTS

| | | |
|---|---|---|
| 5,847,047 A | 12/1998 | Haynie |
| 2011/0195041 A1 | 8/2011 | Chisholm et al. |
| 2012/0018334 A1* | 1/2012 | Baasov ............... A01N 43/60 206/459.5 |
| 2016/0311973 A1 | 10/2016 | Yang et al. |

OTHER PUBLICATIONS

IP.com seach query 202005201711; downloaded May 20, 2020.*
IP.com seach query 202005201725; downloaded May 20, 2020.*
Fournier et al. "Click" Chemistry as a Promising Tool for Side-Chain Functionalization of Polyurethanes. Macromolecules, 2008, 41 (13), pp. 4622-4630.
Bakhshi et al. Polyurethane Coatings Derived from 1,2,3-Triazole-Functionalized Soybean Oil-Based Polyols: Studying their Physical, Mechanical, Thermal, and Biological Properties. Macromolecules 2013, 46, 7777-7788.
Riva et al. Contribution of "click chemistry" to the synthesis of antimicrobial aliphatic copolyester. Polymer (2008), vol. 49, iss. 8, pp. 2023-2028.
Kantheti et al. Synthesis and characterization of triazole rich polyether polyols using click chemistry for highly branched polyurethanes. Reactive and Functional Polymers vol. 73, Issue 12, Dec. 2013, pp. 1597-1605.
Munoz-Bonilla et al. Polymeric materials with antimicrobial activity. Progress in Polymer Science, vol. 37, Issue 2, Feb. 2012, pp. 281-339.
Zeglam et al. Synthesis and Antimicrobial Activity of Some New Phthalimide Derivatives. Asian Journal of Pharmaceutical Analysis and Medicinal Chemistry. 3(3), 2015, 154-161.

* cited by examiner

*Primary Examiner* — Jeffrey T. Palenik
(74) *Attorney, Agent, or Firm* — Christopher S. Dodson; Nexsen Pruet, PLLC

(57) ABSTRACT

In one aspect, the present disclosure relates to click-functional antimicrobial molecules (including small molecules or, in some cases, macromolecules) and the construction of antimicrobial polymers such as polyurethanes, polyesters, and polyacrylates, including through the use of such molecules. In some cases, the antimicrobial click-functional molecules are based on 1,2-benzisothiazolin-3-one (BIT), trimethylguanidine or tetramethylguanidine (TMG), polyhexamethylene guanidine (PHMG), fluorine-containing molecules, or a combination thereof. For example, 1,2-benzisothiazolin-3-one (BIT) functionalized with an alkyne (BIT-Al), trimethylguanidine or tetramethylguanidine (TMG) functioned with an alkyne (TMG-Al) or dual alkynes (TMG-dAl), and/or polyhexamethylene guanidine (PHMG) functionalized with an alkyne (PHMG-Al) are described herein. Clickable antimicrobial polymers can be used to form coatings or films.

18 Claims, 26 Drawing Sheets

Figure 12A
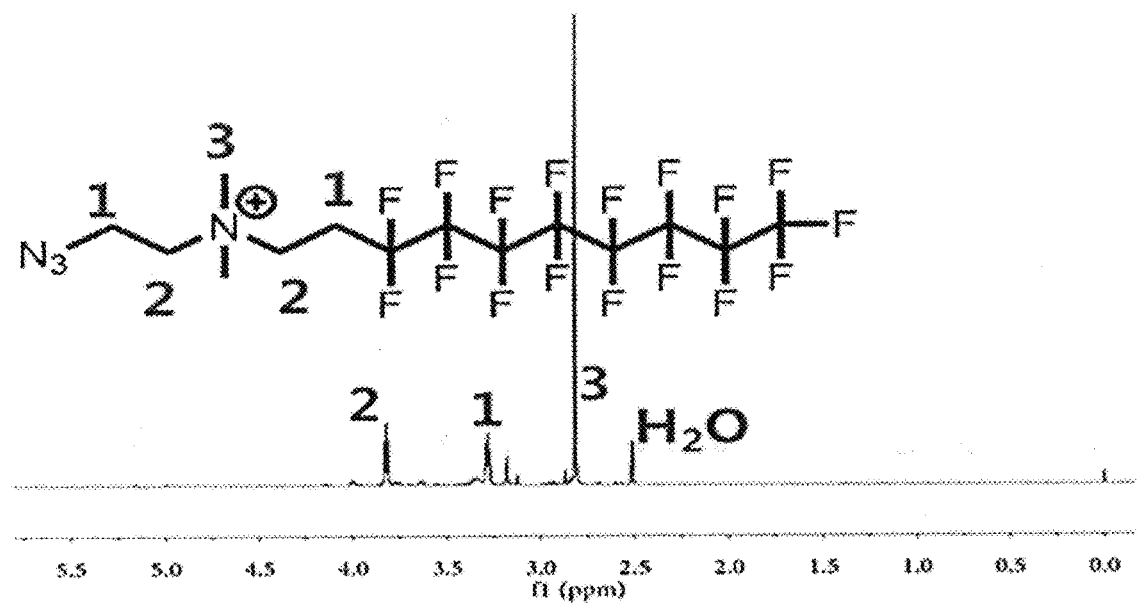
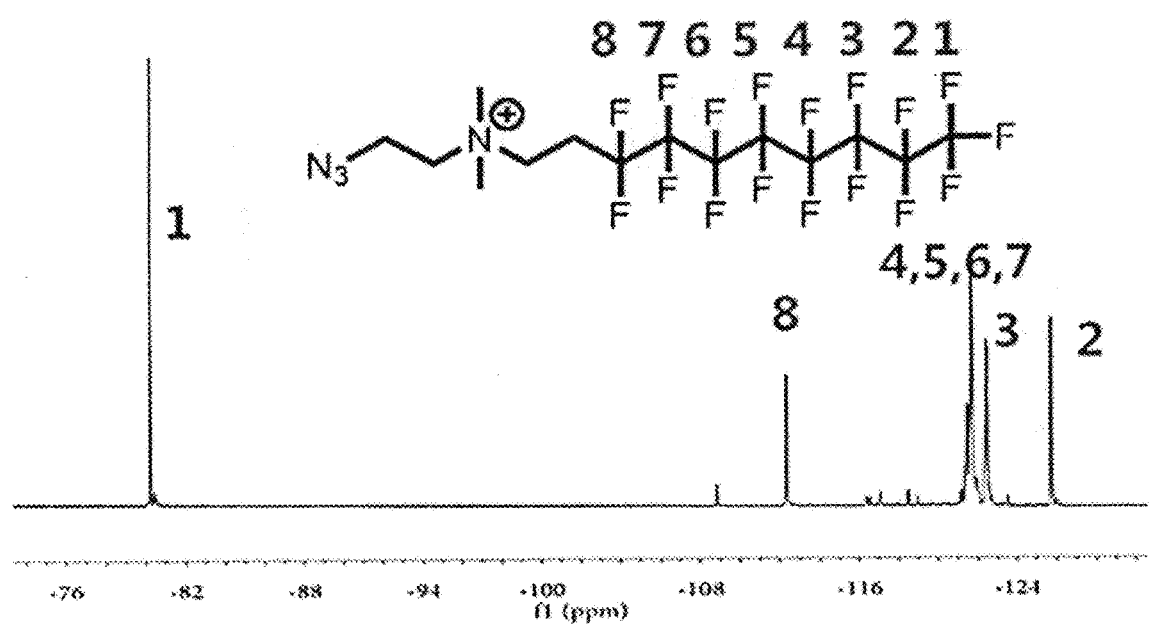
Figure 12C

CLICKABLE ANTIMICROBIAL MOLECULES AND POLYMERS

CROSS REFERENCE TO RELATED APPLICATIONS

This application claims priority pursuant to 35 U.S.C. § 119(e) to U.S. Provisional Patent Application Ser. No. 62/426,668, filed on Nov. 28, 2016, which is hereby incorporated by reference in its entirety.

FIELD

The present disclosure relates to antimicrobial molecules and the construction of antimicrobial polymers such as polyurethanes, polyesters, and polyacrylates.

BACKGROUND

Microbes are everywhere in the world and some of them are positive, but others may be fatal. According to the list of major concerns about health from the World Health Organization (WHO), many health concerns are caused by microorganisms, which contaminate water and sanitation services and infect thousands of people. Therefore, some treatments such as cleaning, disinfection, and sterilization of wastewater and air are necessary. Some natural products or small molecules are used to prevent the spread and growth of microbes, but various unpleasant side effects (such as releasing biocides into the environment) are still significant concerns.

Compared to low molecular weight antibacterial agents, antimicrobial polymers are chemically stable macromolecules with reduced residual toxicity, prolonged lifetime, and improved antimicrobial efficiency. Antimicrobial polymers can be classified into three types: (a) polymeric biocides, (b) biocidal polymers, and (c) biocide-releasing polymers. Siedenbiedel, F.; Tiller, J. C. *Polymers* 2012, 4, 46. In essence, the active ingredients of the polymeric biocides and biocide-releasing polymers are small molecules possessing antimicrobial activity. On the other hand, biocidal polymers can be an effective tool to kill microbes and may be less likely to result in evolved drug resistance. Typical representatives of biocidal polymers are cationic polymers containing quaternary ammonium groups. In terms of evolutionary history, it is difficult for microbes to produce drug resistance to such species because polycations interact with the microbial cells carrying a negative charge.

To obtain permanent, non-leaching antimicrobial polymeric materials, specific antibacterial small molecules (e.g., 1,2-benzisothiazolin-3-one (BIT)) and small or macro cationic molecules (e.g., trimethylguanidine or tetramethylguanidine (TMG) or polyhexamethylene guanidine (PHMG)) can be immobilized to polymers.

For specific antibacterial small molecules, U.S. Pat. No. 9,371,479 discloses a technique for encapsulating a biocide such as BIT into carrier materials. After a predetermined time, biocides are released from the carrier materials and then kill the microbes. U.S. Pat. No. 9,392,786 discloses BIT serving as an ingredient to control pest. But this physically blended BIT material is not environment-friendly and increases the risk of drug resistance.

For small or macro cationic molecules, U.S. Patent Application Publication 2004/0115160 discloses that quaternary ammonium esters are dissolved in water or other solvent for disinfection and preservation of devices. Cationic molecules present antimicrobial properties as they universally interact with negatively charged microbial membranes via electrostatic interactions. A variety of methods were used to fabricate cationic polymers in the antimicrobial field because cationic polymers do not have to interact with specific targets in microbes and can effectively suppress bacterial drug resistance. For example, U.S. Patent Application Publication 2011/0150977 discloses biodegradable cationic block copolymers containing quaternary amine group prepared by ring-opening polymerization (ROP), which can form aqueous mixtures suitable for antimicrobial applications. Through the ROP method, U.S. Patent Application Publication 2012/0251607 and U.S. Patent Application Publication 2012/0251608 also disclose certain antimicrobial polycarbonates containing quaternary amine groups. U.S. Patent Application 2012/0195849 discloses certain novel polymers (SMAMPs) containing a guanidine group or quaternary amine group prepared by ring-opening metathesis polymerization (ROMP), which kill microbes through mimicking the structure of natural antimicrobial peptides (AMPs). U.S. Patent Application Publication 2010/0240799 discloses an application of PHMG in the antimicrobial film. The PHMG serves as film-forming composition via physical blending and also exhibits antimicrobial property. U.S. Pat. Nos. 7,282,538 and 7,531,225 disclose a functional polyolefin master batch containing guanidine salt oligomer by radical initiator. For these methods, physical blending results in quickly reduced bactericidal efficiency over service time due to the diffusion of the physically mixed antimicrobial agents. Polymerization of monomers containing guanidine group or quaternary amine may limit the use of available types and number of cationic monomer, which may also result in the loss of flexibility or range of polymer properties, such as mechanical properties.

Due to the above-mentioned limitations, there still exists an urgent need for an efficient and convenient approach to prepare coating materials with long-lasting antimicrobial properties and to enable fine-tuning of material properties such as mechanical properties.

SUMMARY

In one aspect, the present disclosure relates to new click-functional antimicrobial molecules (including small molecules or, in some cases, macromolecules) and the construction of antimicrobial polymers such as polyurethanes, polyesters, and polyacrylates, including through the use of such molecules. In some cases, the antimicrobial click-functional molecules are based on 1,2-benzisothiazolin-3-one (BIT), trimethylguanidine or tetramethylguanidine (TMG), polyhexamethylene guanidine (PHMG), fluorine-containing molecules, or a combinations thereof. For example, 1,2-benzisothiazolin-3-one (BIT) functioned with an alkyne (BIT-Al), trimethylguanidine or tetramethylguanidine (TMG) functioned with an alkyne (TMG-Al) or dual alkynes (TMG-dAl) and polyhexamethylene guanidine (PHMG) functioned with an alkyne (PHMG-Al) are described herein.

As understood by one of ordinary skill in the art, a "clickable" moiety or a "click-functional" species is a moiety or species that can participate in a so-called "click chemistry" reaction, such as an azide-alkyne cycloaddition reaction or a thiol-ene reaction. For instance, a clickable moiety can include an azide or alkyne moiety. Similarly, a click-functional species can be a chemical species that includes, somewhere in the species, one or more clickable moieties. As described further hereinbelow, a click-functional species can and generally does include moieties other than the one or more clickable moieties of the species.

The present disclosure also provides a facile method to prepare antimicrobial polymers containing clickable functional groups. For instance, quaternary ammonium groups can be readily incorporated into the polymers and used as antimicrobial active moieties, and clickable quaternary ammonium functional groups can be incorporated and used to link different functional molecules to the polymers. Quaternary ammonium polymers described herein containing clickable functional group are effective antimicrobial agents. Moreover, in some cases, the antimicrobial activity of the polymers is effectively increased with the use of fluorine-containing molecule via click chemistry. Thus, in another aspect, the present disclosure relates to introducing fluorine-containing small molecules; 1,2-benzisothiazolin-3-one (BIT); trimethylguanidine or tetramethylguanidine (TMG); or polyhexamethylene guanidine (PHMG) into polymers to improve the antimicrobial properties of the polymers through a click reaction between the clickable polymer platforms and the clickable antimicrobial small molecule/macro cationic molecules. Further, in some embodiments, polymers having improved mechanical properties as well as improved antimicrobial properties are described herein. For example, in some cases, TMG-dAl is used to attach a TMG moiety to a "clickable" polymer, wherein TMG-dAl is trimethylguanidine or tetramethylguanidine functionalized with dual alkynes. The guanidinium cations and the alkyne moieties, respectively, introduce an antimicrobial property to the clickable polymer and also enhance the mechanical properties of the clickable polymer.

The present disclosure also provides a facile way to synthesize a diol monomer containing a quaternary ammonium group and a clickable functional group. For example, in some embodiments, new functional diols that contain an anti-microbial tertiary amine and clickable alkyne are disclosed herein. These diols can be used as a "diol" reactant in many polymer syntheses to confer antimicrobial properties to polymers such as polyurethanes, polyesters, and polyacrylates.

In still another aspect, the present disclosure further provides new small molecules containing a quaternary ammonium group, fluorine, and clickable azide group.

As described further hereinbelow, the objectives of this disclosure relating to polymers containing 1,2-benzisothiazolin-3-one (denoted as "PU-BIT"), polymers containing trimethylguanidine or tetramethylguanidine (PU-TMG), and polymers containing polyhexamethylene guanidine (PU-PHMG) are achieved, in some cases, through introducing small molecular clickable monomers into polymer side chains to produce antimicrobial polymers with specific antimicrobial small molecule or non-specific (broad spectrum) small/macro cationic molecules. The clickable small molecular monomers include, for example, BIT with alkyne, TMG with alkyne, and PHMG with alkyne, which can be introduced into polymer side chains by click chemistry, for example the copper (I)-catalyzed alkyne-azidecycloaddition (CuAAC).

Thus, objectives of the present disclosure include the following: provide compositions useful as antimicrobial material and coating; provide methods for using compositions useful as antimicrobial material and coating; provide compositions useful in contact antimicrobial surfaces; provide compositions useful in preserving a material's surface from contamination; provide a facile method to prepare clickable antimicrobial polymers and antimicrobial monomers containing quaternary ammonium group and clickable functional group; and provide a method to improve the antimicrobial activity by the use of fluorine-containing molecule via click chemistry.

In some embodiments, compounds consistent with the foregoing are described herein. In some such instances, a compound described herein has the structure of Formula (I):

(I)

wherein $R_1$ comprises an antimicrobial moiety or a dehydrogenated antimicrobial moiety. For example, in some cases, $R_1$ comprises trimethylguanidine or tetramethylguanidine (TMG) or dehydrogenated TMG. An "antimicrobial" moiety or composition, for reference purposes herein, is any moiety or composition that has antimicrobial activity, such as indicated by an antimicrobial rate described herein. More particularly, an antimicrobial moiety or composition described herein can have an antimicrobial rate of, or reduce microbial proliferation (such as bacterial proliferation) by, at least 20%, at least 30%, at least 40%, at least 50%, at least 60%, at least 70%, at least 80%, at least 90%, at least 95%, or at least 99%, relative to a negative control. In some cases, an antimicrobial moiety or composition described herein has an antimicrobial rate or reduces microbial proliferation such as bacterial proliferation by 20-100%, 20-80%, 20-60%, 40-100%, 40-99%, 40-90%, 50-99%, 50-90%, 50-80%, 60-99%, 60-95%, 60-85%, 60-75%, 70-100%, 70-95%, 70-90%, 80-99%, or 80-90%, relative to a negative control. Further, in some embodiments, an antimicrobial moiety or composition described herein can kill and/or reduce the proliferation of both Gram-positive bacteria and Gram-negative bacteria. Additionally, in some instances, an antimicrobial moiety or composition described herein can kill and/or reduce the proliferation of microbes over a sustained period of time, such as a period of up to 6 months, up to 3 months, up to 2 months, or up to 1 month. In some cases, the period of time is 1 week to 6 months, 1 week to 3 months, or 1 week to 1 month. Non-limiting examples of antimicrobial moieties, as described further herein, include moieties having a quaternary nitrogen/ammonium group. An antimicrobial moiety described herein can also include a fluorinated hydrocarbon.

Moreover, turning again to Formula (I), in some cases, $R_1$ is joined to the HC≡C—($CH_2$)— moiety of the structure of Formula (I) through a nitrogen-carbon bond. For example, in some instances, the compound having the structure of Formula (I) comprises Compound (I-1) or Compound (I-2):

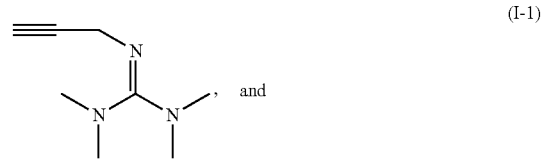
(I-1)

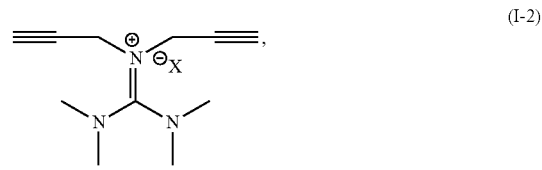
(I-2)

wherein X⁻ is a monovalent anion. Any monovalent anion not consistent with the objectives of the present disclosure may be used. For example, as described further below, in some cases the monovalent anion is a halide anion, such as chloride, bromide, or iodide. In other instances, the monovalent anion is a complex or multi-atom monovalent anion, such as $BF_4^-$.

In other embodiments, a compound described herein has the structure of Formula (II):

$$N_3-R_2 \quad (II),$$

wherein $R_2$ comprises an antimicrobial moiety or an antimicrobial moiety in which a leaving group of the antimicrobial moiety has been replaced with the azido group of the structure of Formula (II). As understood by one of ordinary skill in the art, a "leaving group" of the antimicrobial moiety is any atom, ion, or other moiety that is displaced or replaced by an azido group during the course of a reaction for modifying the antimicrobial moiety to include an azido group. Some exemplary reactions and leaving groups are described further hereinbelow. Turning again to Formula (II), in some cases, $R_2$ comprises a fluorinated hydrocarbon moiety and/or a quaternary ammonium moiety. In addition, in some embodiments, the fluorinated hydrocarbon moiety is joined to the $N_3$— moiety of the structure of Formula (II) through the quaternary ammonium moiety. For instance, a compound described herein can have the structure of Formula (II-1):

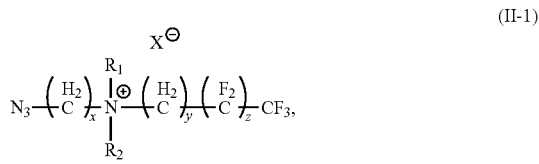

wherein $R_1$ and $R_2$ are each independently a linear or branched C1-C20 alkyl, alkenyl, aryl, or heteroaryl group; wherein X⁻ is a monovalent anion (such as described above); and wherein x, y, and z are each independently an integer from 1 to 20. As understood by one of ordinary skill in the art, a "C1-C20" group described herein has 1 to 20 carbon atoms.

In still other embodiments, a compound described herein has the structure of Formula (III):

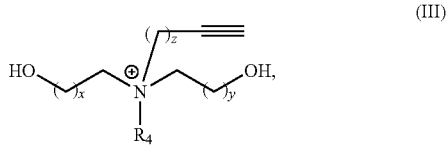

wherein $R_4$ is a linear or branched C1-C20 alkyl, alkenyl, aryl, or heteroaryl group; and x, y, and z are each independently an integer from 1 to 20.

In another aspect, compositions are described herein, wherein the composition comprises a polymer or oligomer formed from a reaction product of (i) a compound having any of the Formulas described hereinabove and (ii) one or more second monomers that react with the compound of (i) to form the polymer or oligomer. In some cases, the one or more second monomers comprise one or more diisocyanates. The use of a diisocyanate may be especially preferred when the compound of the foregoing Formulas is a diol that can react with the diisocyanate to form a polyurethane. Other second monomers may also be used. Additional monomers (e.g., third, fourth, and/or fifth monomers) may also be used to form a reaction product described herein. For instance, in some cases, a polymer or oligomer described herein is a reaction product of (i) and (ii) above as well as (iii) a chain extender and/or (iv) a crosslinker. A "chain extender," as understood by one of ordinary skill in the art, can have two reactive groups operable to link or crosslink a polymer, such as a polyurethane. In some cases, a chain extender described herein is a diol, such as ethylene glycol, 1,4-butanediol (1,4-BDO or BDO), 1,6-hexanediol, cyclohexane dimethanol, or hydroquinone bis(2-hydroxyethyl) ether (HQEE). A "crosslinker" can include more than two reactive groups operable to crosslink the polymer. Further, in some embodiments, a polymer or oligomer described herein is a reaction product of (i), (ii), optionally (iii) and/or (iv), and also (v) a polymerizable antimicrobial moiety, such as a diol including a quaternary ammonium portion. It is further to be understood that (v) and (i) may be the same or different species. It is further to be understood that, in some cases, (i) is at least partially replaced with a diol not according to the Formulas described above. For instance, a polymeric or oligomeric diol such as a polyalkylene glycol may be used to initially form the polymer through reaction with the diisocyanate, and then a species according to one of the Formulas described above can be subsequently or simultaneously added as a separate component. Additionally, in some instances, the polymer or oligomer comprises a quaternary ammonium moiety within a backbone of the polymer or oligomer, and the polymer or oligomer is antimicrobial. Moreover, in some embodiments, the polymer or oligomer of a composition described herein forms an antimicrobial coating or film on a surface. Any surface not inconsistent with the objectives of the present disclosure may be coated with a polymer or oligomer or composition described herein. For example, in some cases, the surface is an exterior surface of a medical device or implant. In other instances, the surface is an exterior surface of a work space, piece of furniture, fixture, or textile. The surface can also be a leather, wood, plastic, or metal surface. Other surfaces may also be used, and the precise surface is not particularly limited. Moreover, as described above, in some embodiments, the surface is formed from an organic material such as an organic polymeric material. In other cases, the surface is formed from an inorganic material such as an elemental metal, metal alloy, or metal mixture (such as stainless steel), or a metal oxide (such as silicon dioxide).

In still another aspect, methods of reducing microbial proliferation on a surface are described herein. In some embodiments, such a method comprises disposing a composition described herein on the surface.

These and other embodiments are described in more detail in the detailed description which follows.

BRIEF DESCRIPTION OF THE FIGURES

FIGS. 12A-D show the $^1$H NMR spectra, carbon NMR ($^{13}$C NMR) spectra, fluorine NMR ($^{19}$F NMR) spectra, and FTIR spectra of clickable small molecules with azide group, fluorine, and quaternary ammonium group, which are described in Example 4. The successful synthesis verified by the $^1$H NMR peaks of protons on —CH$_2$—CH$_2$—N$^+$— (δ 3.82 ppm, t), N$_3$—CH$_2$—CH$_2$— (δ 3.28 ppm, t) and —N$^+$(CH$_3$)$_2$— (δ 2.81 ppm, s) in FIG. 12A, and the appearance of the $^{13}$C NMR peaks at δ 56.28, δ 45.74 and δ 44.04, and the $^{19}$F NMR peaks of fluorines on —CF$_3$ (δ −80.18 ppm), —CH$_2$—CF$_2$— (δ −112.35 ppm) and CF$_3$CF$_2$— (δ −125.73 ppm) in FIG. 12C, and the characteristic infrared absorption peaks at around 2106 cm$^{-1}$ for —N$_3$ and around 1209 cm$^{-1}$, 1153 cm$^{-1}$ for —CF$_2$— in FIG. 12D.

FIG. 22 shows antibacterial activity of polyurethane with quaternary ammonium group and fluorine (PU-F) against the

*Escherichia coli*, which is synthesized from PU-Al (wt. %=0.94%). According to the results, PU-F killed all the *Escherichia coli* when the mass percent of clickable small molecule with quaternary ammonium group and fluorine in the polymer (PU-F) is 1.05%. PU-F has no obvious antimicrobial effect when the mass percent of clickable small molecule in the polymer (PU-F) is 0.71%.

Figure 23:
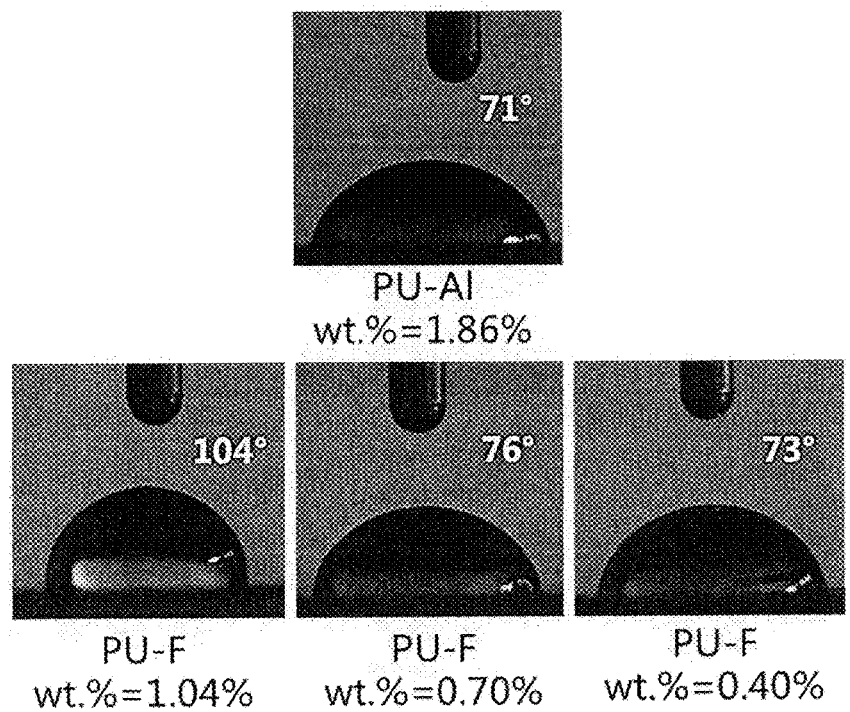

FIG. 23 shows the sessile contact angle of clickable polyurethane with quaternary ammonium group and side-chain alkyne (PU-Al, wt. %=1.86%) polyurethane with quaternary ammonium group and fluorine (PU-F, wt. %=1.04%, wt. %=0.70% or wt. %=0.40%). The contact angle of PU-Al is 71°, while the contact angle of PU-F increases with the increasing of fluorine content. The contact angle of PU-F reaches 104° when the mass percent of clickable small molecule with quaternary ammonium group and fluorine in the polymer (PU-F) is 1.04%.

Figure 24:
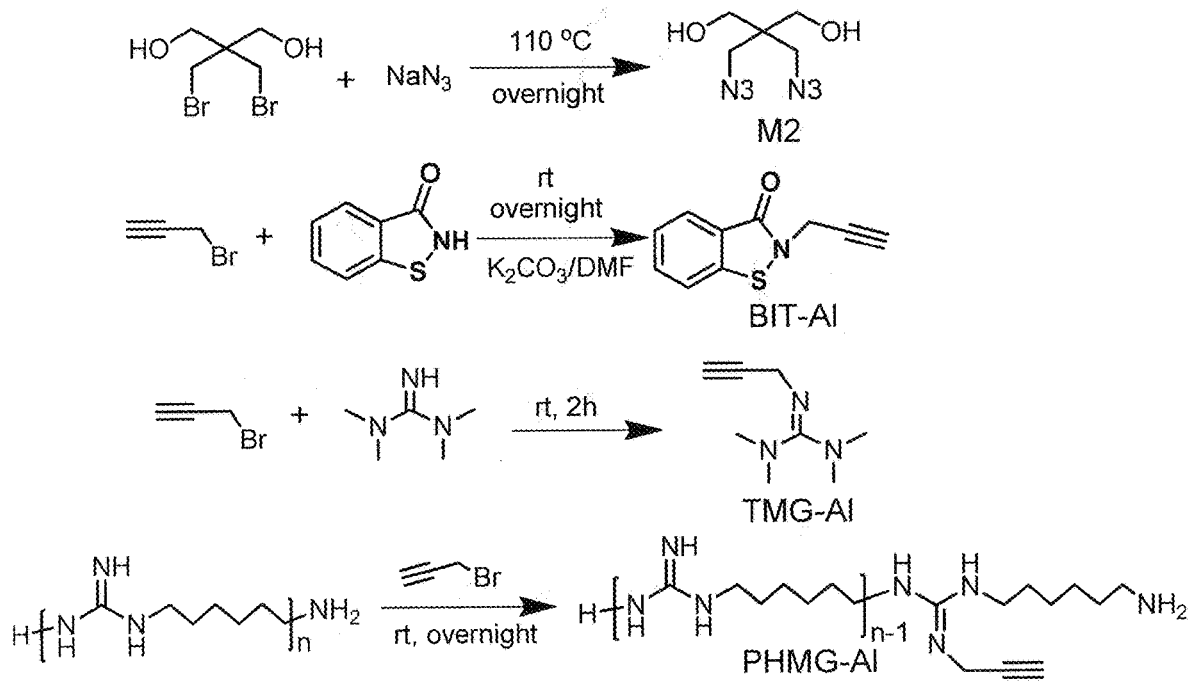

FIG. 24 shows a series of schemes representing the synthesis of clickable diols with azide groups (M2) and monomers with alkyne (BIT-Al, TMG-Al, TMG-dAl and PHMG-Al), which are suitable for preparing clickable waterborne polymers via step-growth polymerization or reacting with azide group through the copper(I)-catalyzed alkyne-azide cycloaddition (CuAAC). This figure is consistent with the embodiments of Examples 5, 6 and 7.

Figure 25:
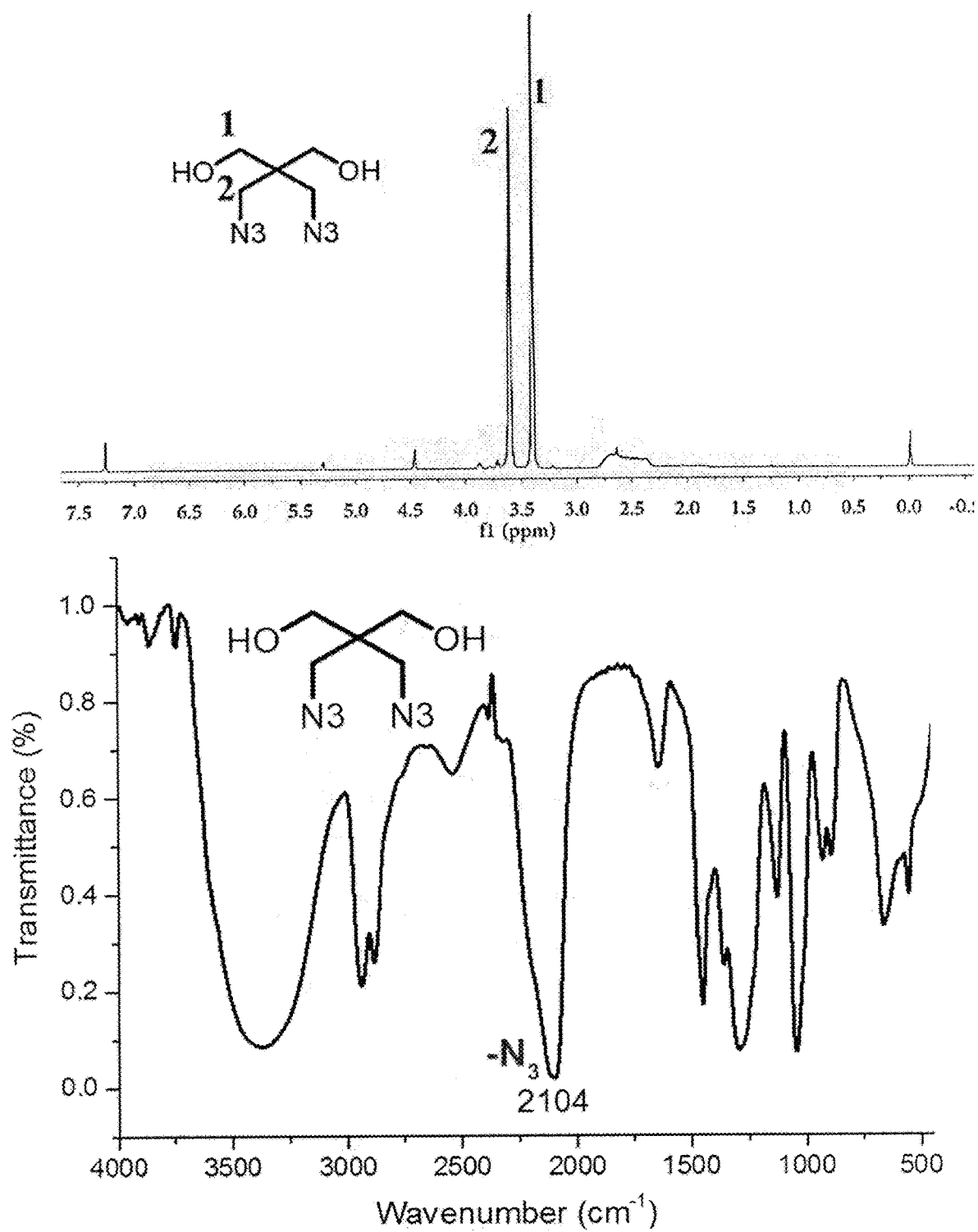

FIG. 25 shows $^1$H NMR spectra and the FTIR spectra of clickable diols with azide groups which are synthesized in Example 1. The successful synthesis of clickable diols with azide groups was confirmed by the appearance of the characteristic infrared absorption peak of azide group at 2104 cm$^{-1}$ and the left shift of the peak of protons on CH$_2$— link to azide groups (around 3.75 ppm) compared to the protons on CH$_2$— link to bromine groups on the starting material, 2,2-bis(bromomethyl)propane-1,3-diol (3.22 ppm).

Figure 26:
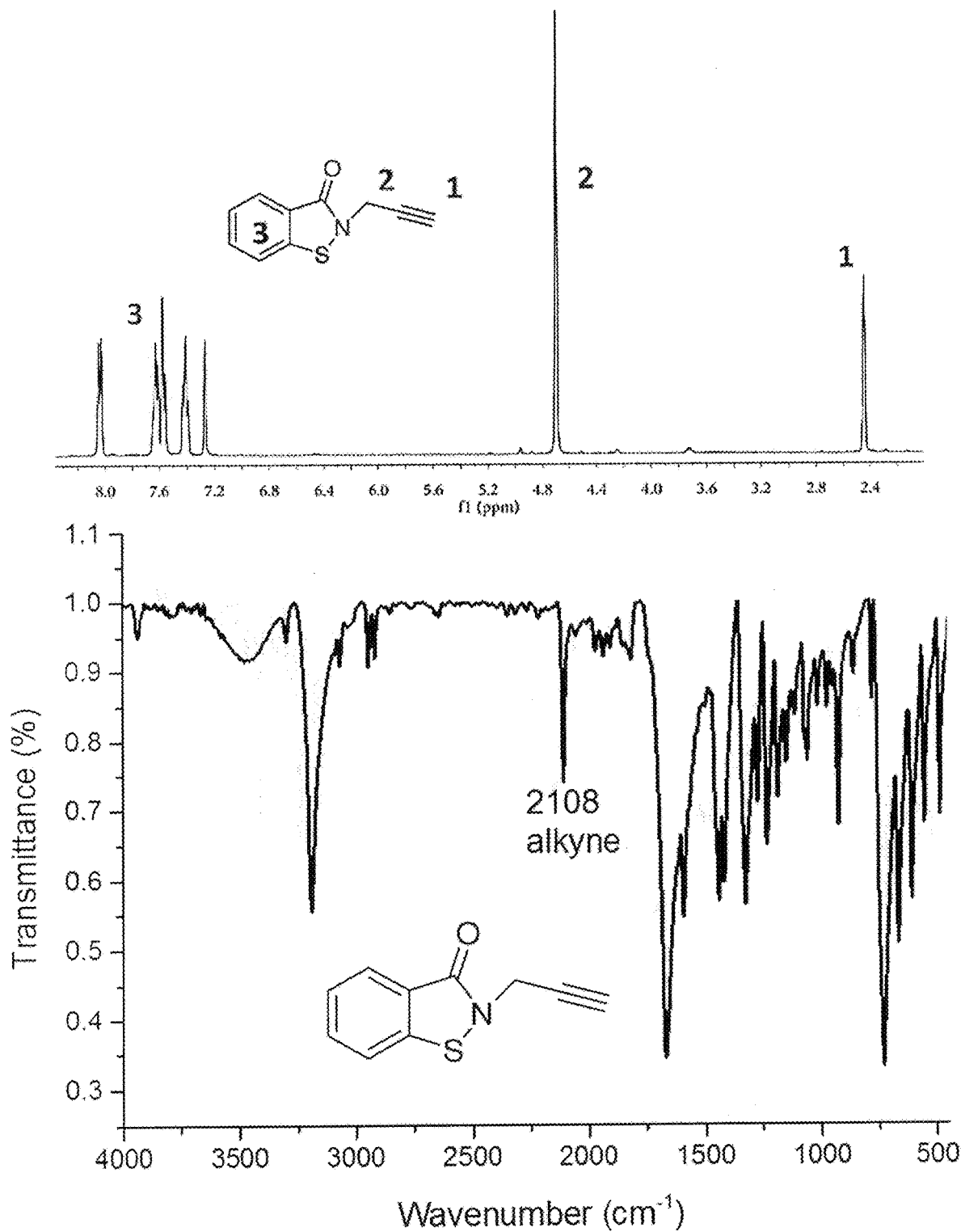

FIG. 26 shows $^1$H NMR spectra and the FTIR spectra of antimicrobial monomer with alkyne (BIT-Al), synthesized in Example 5. The successful synthesis of TMG-Al was confirmed by the appearance of the characteristic infrared absorption peak of alkyne group at 2108 cm$^{-1}$ and the $^1$H NMR peaks of protons on —CH$_2$—C≡CH (δ 2.45 ppm, s), —CH$_2$—C≡CH (δ 4.69 ppm, s) and Ar (δ 7.37~8.10 ppm, m).

Figure 27:
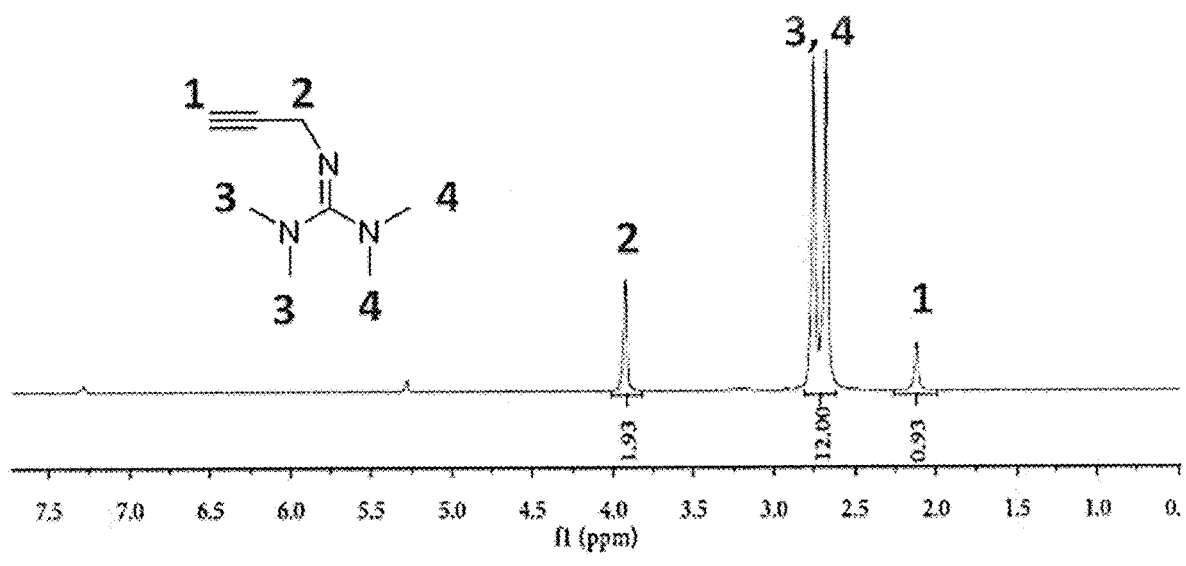
Figure 27:
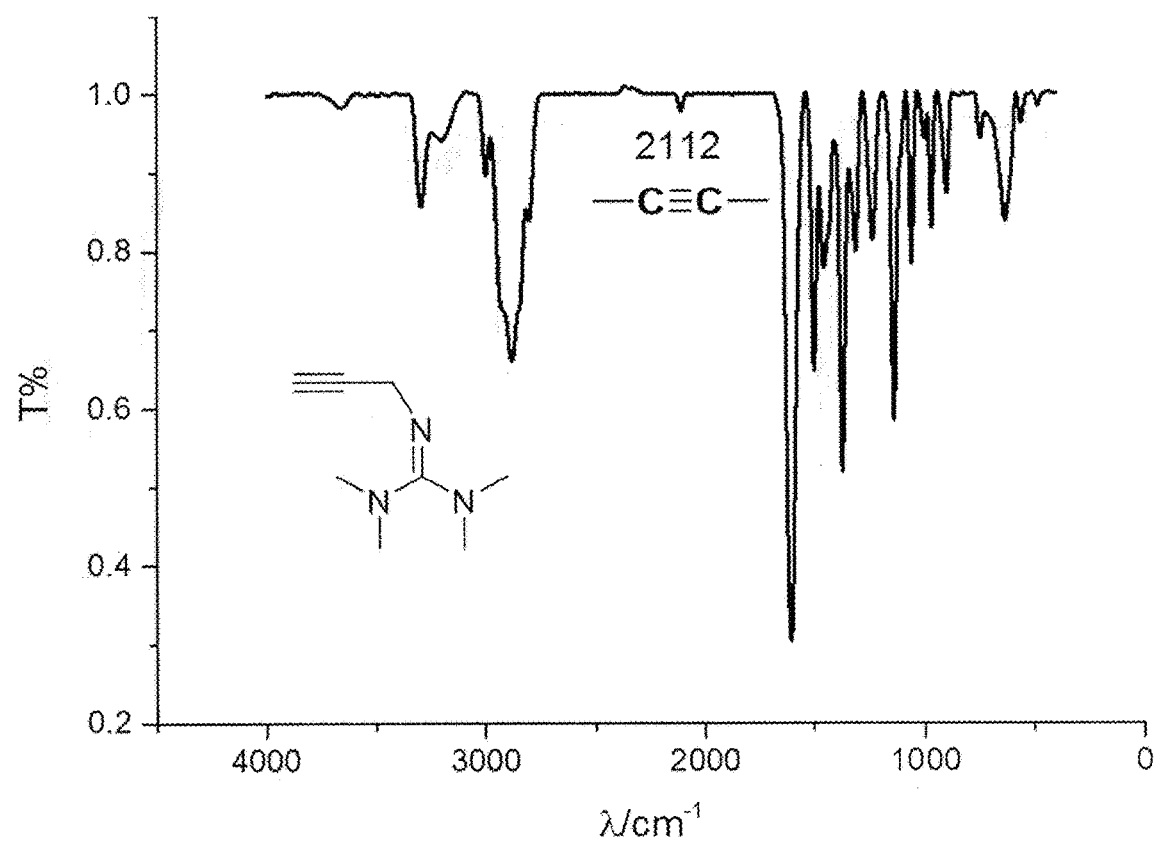

FIG. 27 shows $^1$H NMR spectra and the FTIR spectra of monomer with alkyne (TMG-Al), as synthesized in Example 6. The successful synthesis of TMG-Al was confirmed by the appearance of the characteristic infrared absorption peak of alkyne group at 2112 cm$^{-1}$ and the $^1$H NMR peaks of protons on —CH$_2$—C≡CH (δ 2.12 ppm, s), —N(CH$_3$)$_2$ (δ 2.67 ppm, s), —N(CH$_3$)$_2$ (δ 2.75 ppm, s) and —CH$_2$—C≡CH (δ 3.92 ppm, s).

Figure 28:
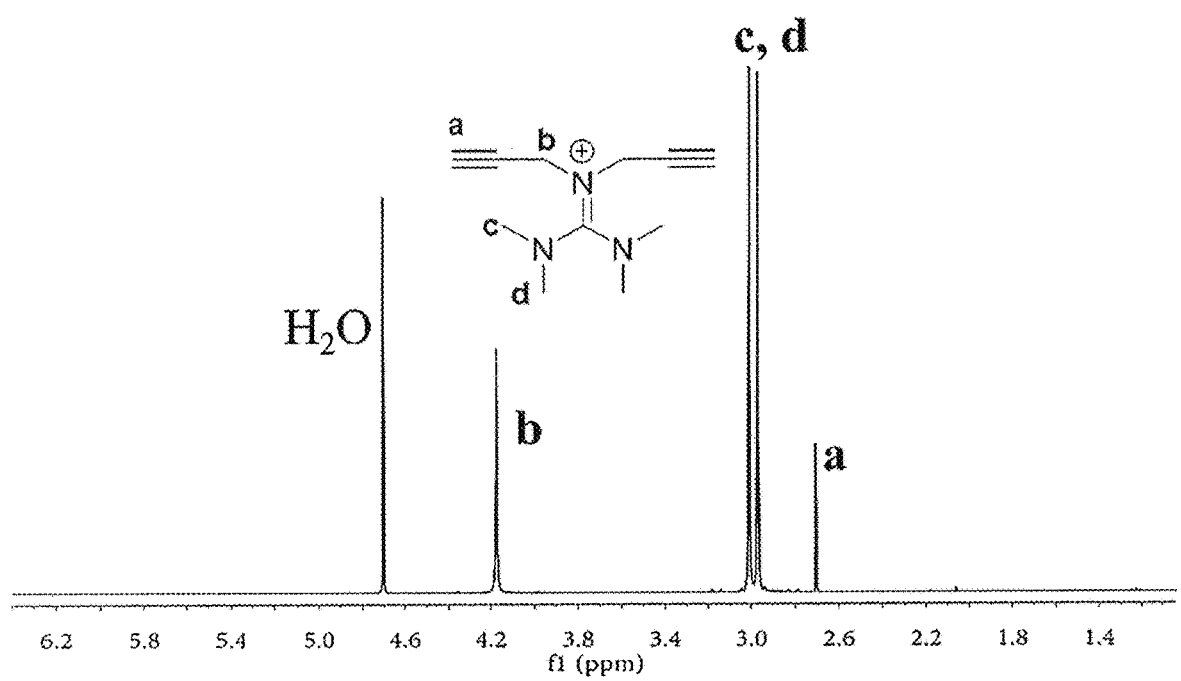

FIG. 28 shows $^1$H NMR spectra of monomer with two alkynes (TMG-dAl). The successful synthesis of TMG-dAl was confirmed by the appearance of the $^1$HNMR peaks of protons on —CH$_2$—C≡CH (δ 2.71 ppm, s), —N(CH$_3$)$_2$ (δ 2.97 ppm, s), —N(CH$_3$)$_2$ (δ 3.00 ppm, s) and —CH$_2$—C≡CH (δ 4.17 ppm, s).

Figure 29:
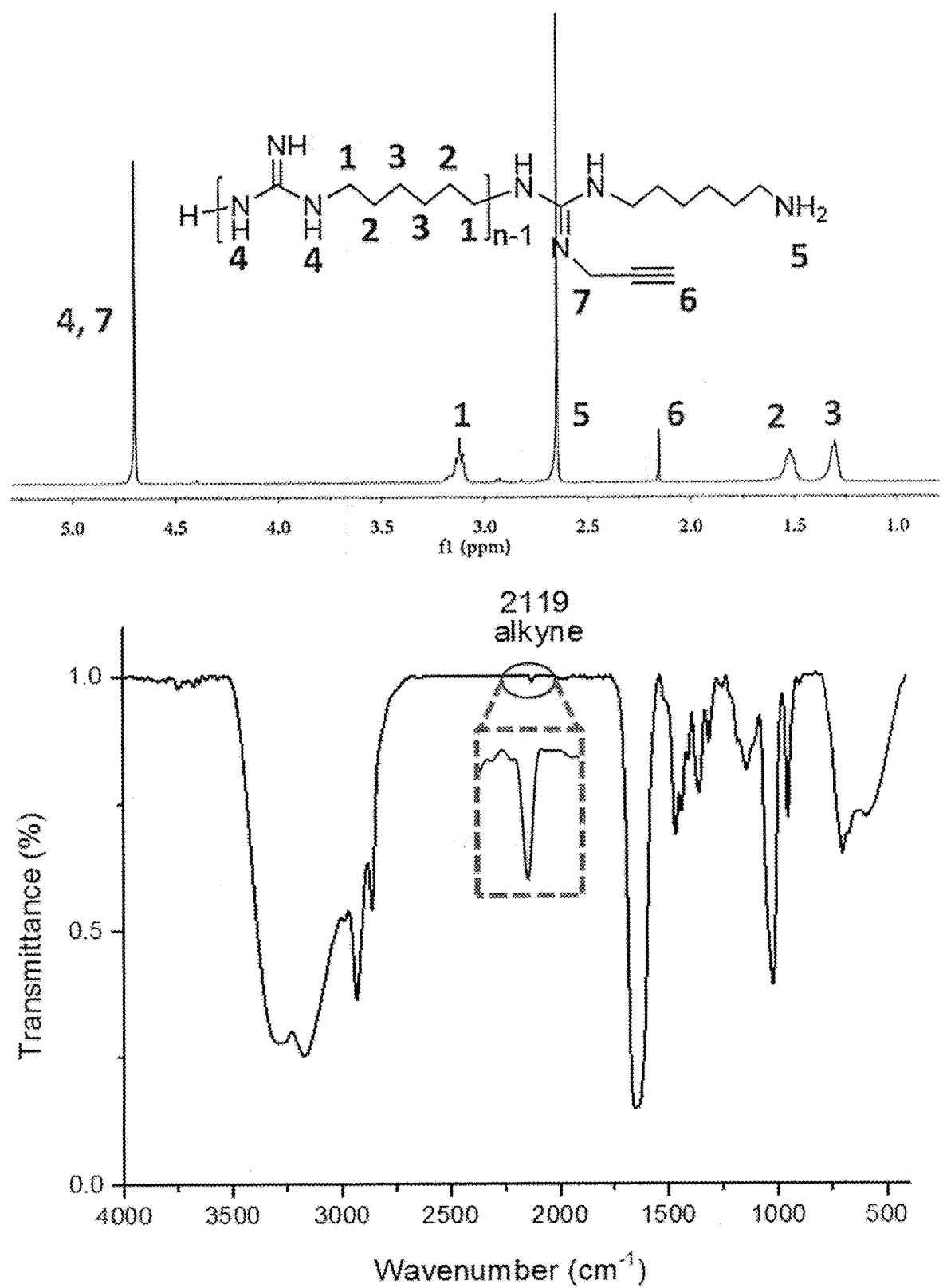

FIG. 29 shows $^1$H NMR spectra and the FTIR spectra of antimicrobial monomer with alkyne (PHMG-Al), as synthesized in Example 8. The successful synthesis of TMG-Al was confirmed by the appearance of the characteristic infrared absorption peak of alkyne group at 2119 cm$^{-1}$ and the $^1$H NMR peaks of protons on —CH$_2$—C≡CH (δ 2.16 ppm), —N(CH$_2$)$_6$N— (δ 1.30 ppm, 1.52 ppm and 2.65 ppm) and —NHC(NH)NH— (δ 4.7 ppm).

Figure 30:
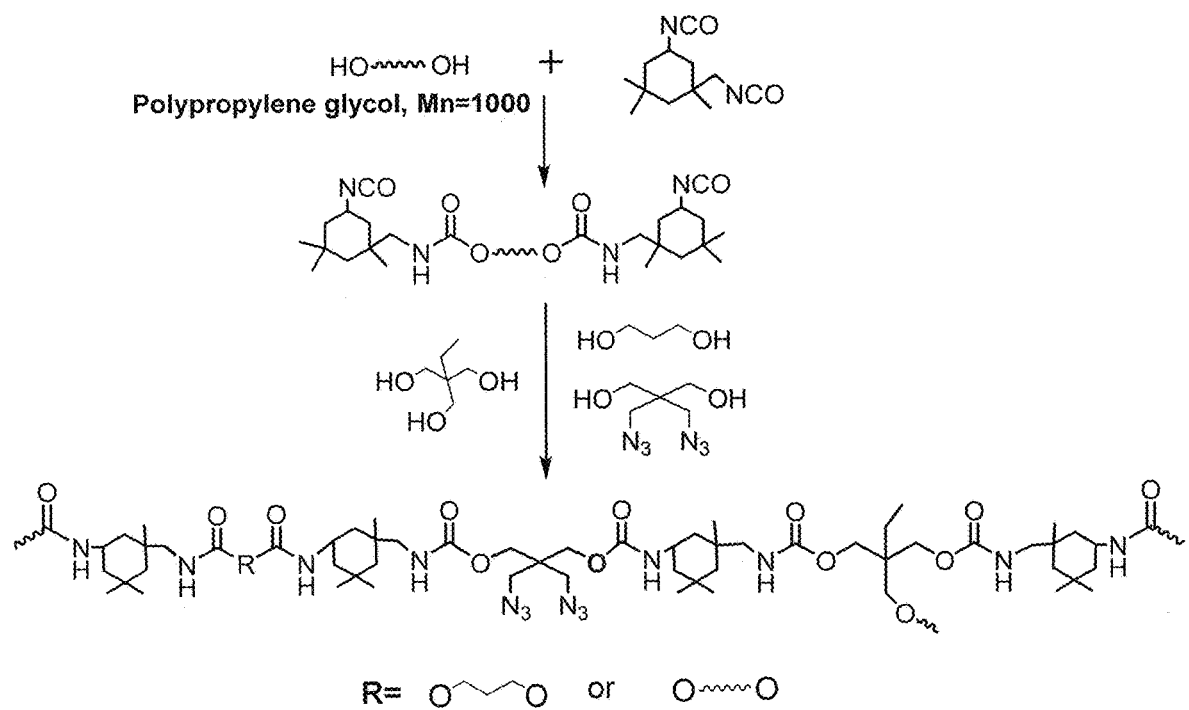

FIG. 30 shows the synthesis of clickable polyurethane with side-chain azide (PU-N$_3$) via step-growth polymerization. This figure is consistent with the embodiment of Example 2.

Figure 31:
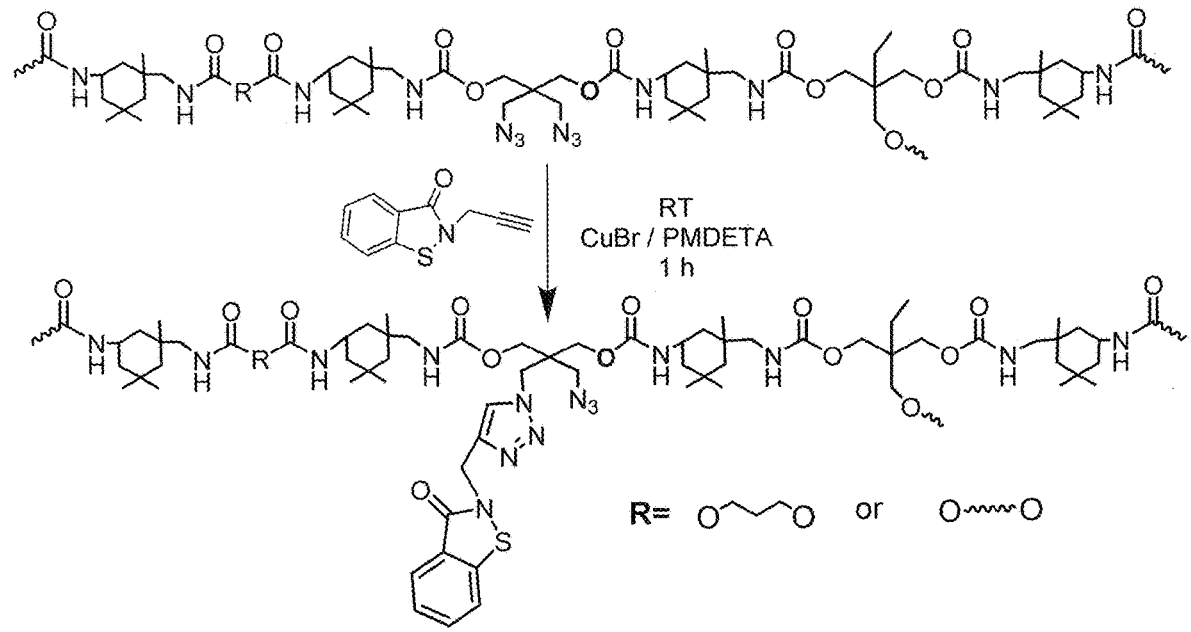

FIG. 31 shows the synthesis of polyurethane containing 1,2-Benzisothiazolin-3-one (PU-BIT) through copper(I)-catalyzed alkyne-azide cycloaddition (CuAAC). This figure is consistent with the embodiment of Example 10.

Figure 32:
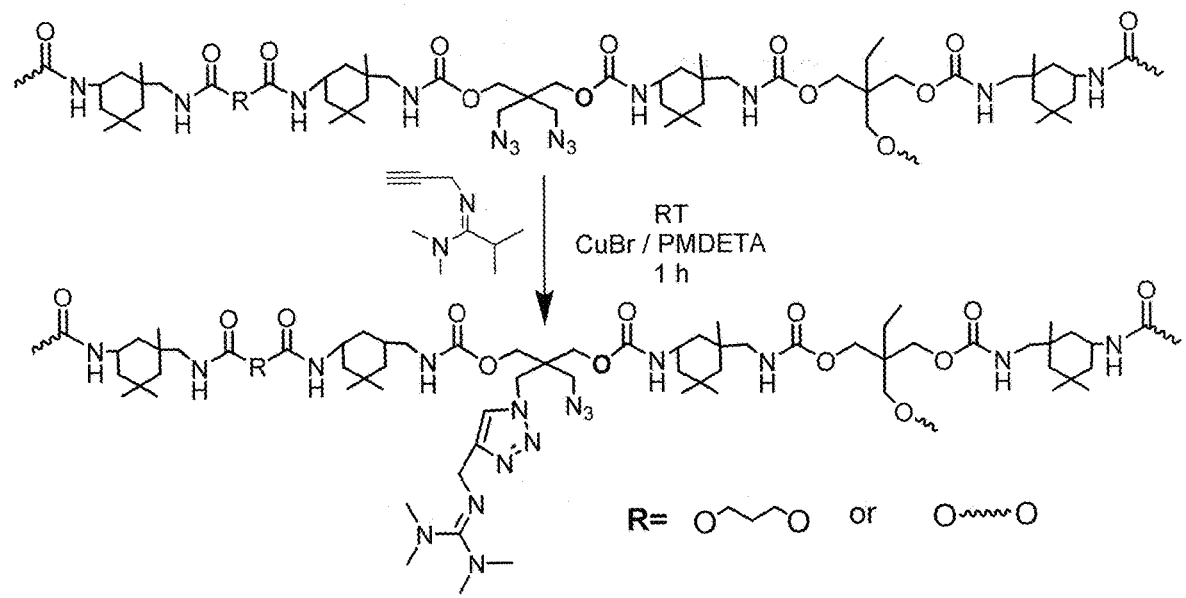

FIG. 32 shows the synthesis of polyurethane containing trimethylguanidine (PU-TMG or PU-dTMG) through copper(I)-catalyzed alkyne-azide cycloaddition (CuAAC). This figure is consistent with the embodiments of Examples 11 and 12.

Figure 33:
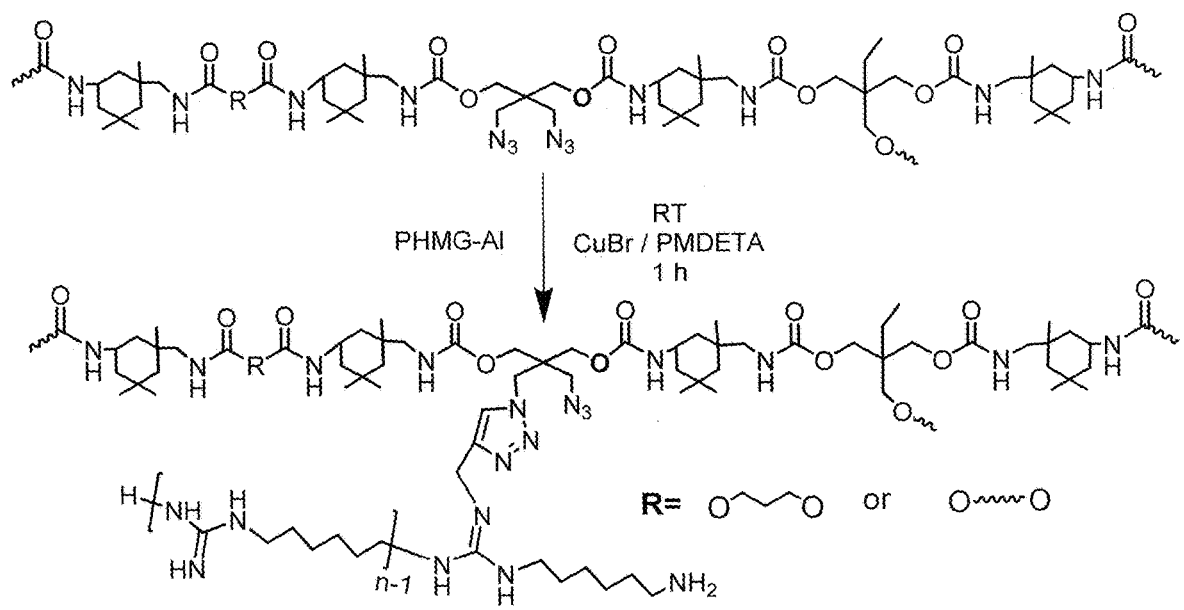

FIG. 33 shows the synthesis of polyurethane containing polyhexamethylene guanidine (PU-PHMG) through copper (I)-catalyzed alkyne-azide cycloaddition (CuAAC). This figure is consistent with the embodiment of Example 13.

Figure 34:
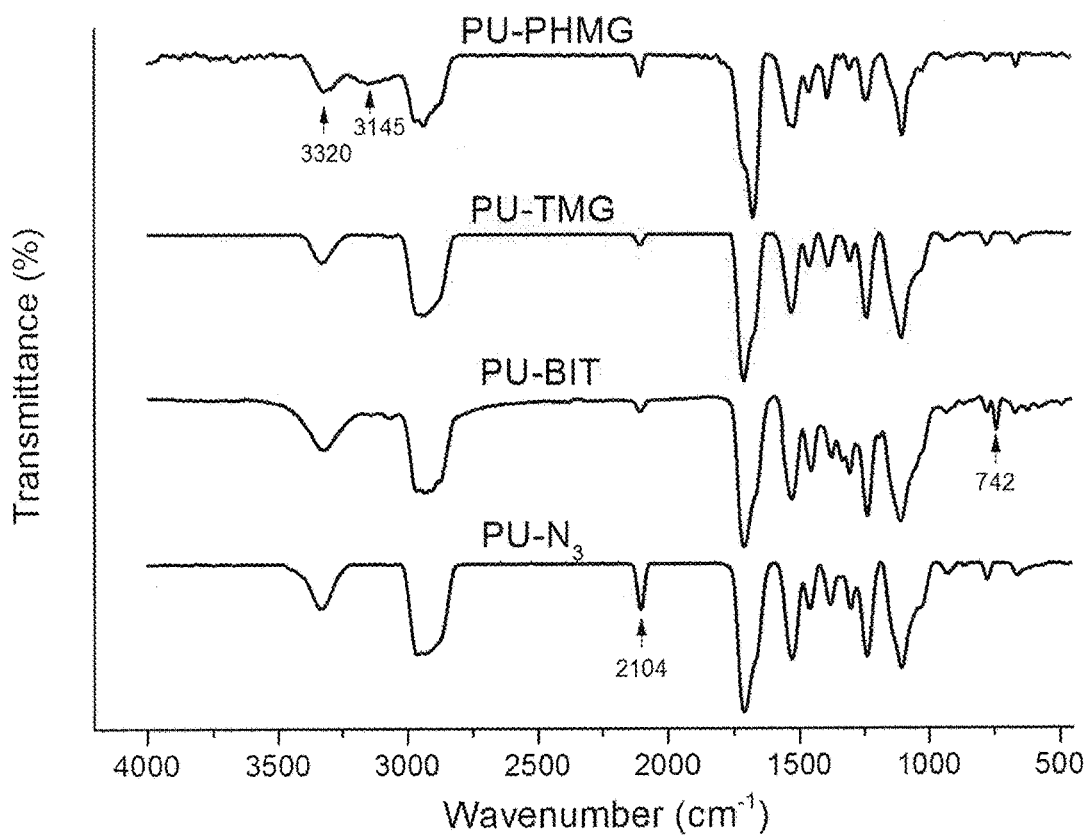

FIG. 34 shows the FTIR spectra of clickable polyurethane with side-chain azide (PU-N$_3$), polyurethane containing 1,2-Benzisothiazolin-3-one (PU-BIT), polyurethane containing trimethylguanidine (PU-TMG or PU-dTMG) and polyurethane containing polyhexamethylene guanidine (PU-PHMG), synthesized as described in Examples 3, 10, 11, 12 and 13. The successful synthesis of PU-N$_3$ was confirmed by the appearance of the characteristic infrared absorption peak of azide group at 2104 cm$^{-1}$. The successful syntheses of PU-BIT, PU-TMG and PU-PHMG were verified by the decrease of the characteristic infrared absorption peak at 2104 cm$^{-1}$ and other evidence, such as C—H bending vibration of ortho-disubstituted benzene in BIT at 742 cm$^{-1}$ or N—H stretching vibration of PHMG at around 3145 cm$^{-1}$.

Figure 35:
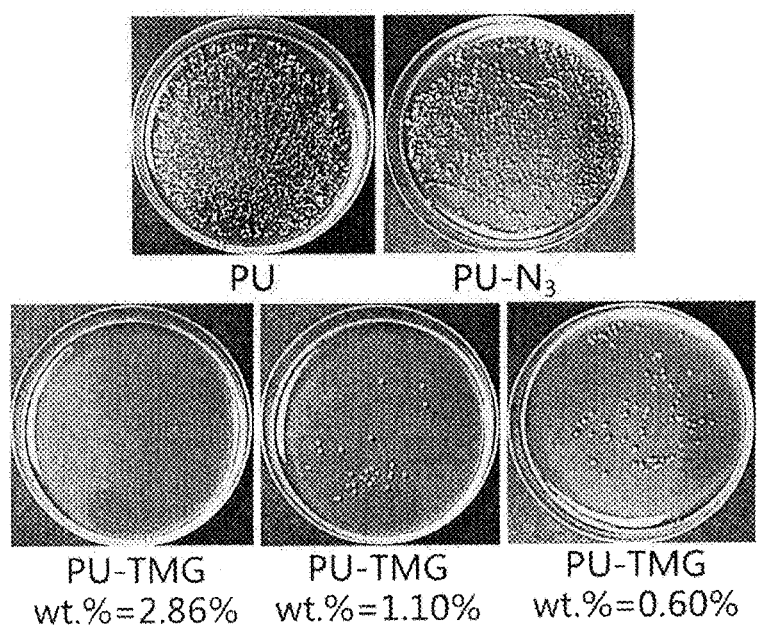

FIG. 35 shows antibacterial activity of polyurethane containing trimethylguanidine (PU-TMG) against the *Staphylococcus aureus*. According to the results, PU-TMG killed all the *Staphylococcus aureus* when the monomers with alkyne (TMG-Al) in the polymer (PU-TMG) is 2.86% by weight. Antibacterial rate of PU-TMG is 97% when the mass percent of TMG-Al in the polymer (PU-TMG) is 1.10%. Antibacterial rate of PU-TMG is also up to 92% when the mass percent of TMG-Al in the polymer (PU-TMG) is 0.60%.

Figure 36:
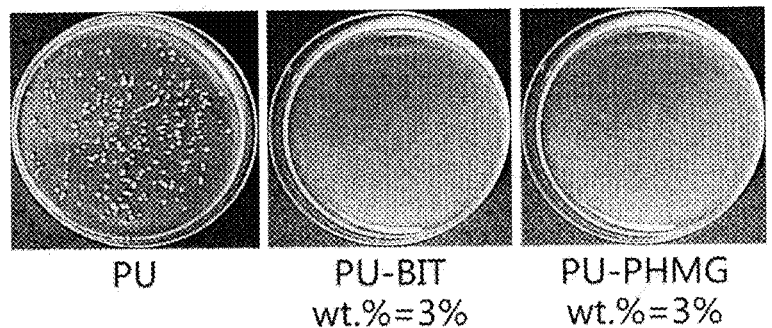

FIG. 36 shows antibacterial activity of polyurethane containing 1,2-Benzisothiazolin-3-one (PU-BIT) and polyhexamethylene guanidine (PU-PHMG) against the *Staphylococcus aureus*. According to the results, PU-BIT and PU-PHMG killed all the *Staphylococcus aureus* when the monomers with alkyne (BIT-Al or PHMG-Al) in the polymer (PU-BIT or PU-PHMG) is 3.00%.

Figure 37:
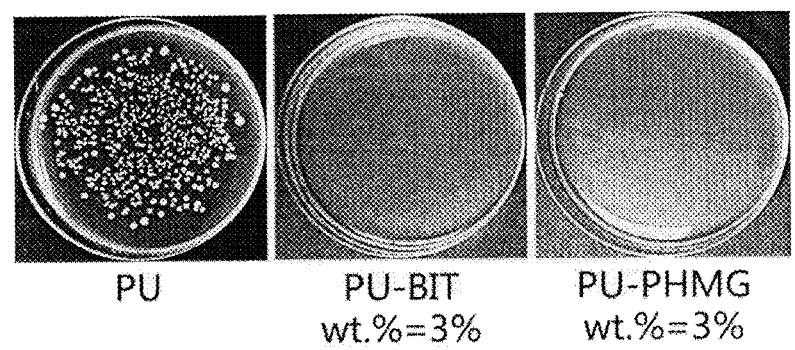

FIG. 37 shows antibacterial activity of polyurethane containing 1,2-Benzisothiazolin-3-one (PU-BIT) and polyhexamethylene guanidine (PU-PHMG) against the *Escherichia coli*. According to the results, PU-BIT and PU-PHMG killed all the *Escherichia coli* when the monomers with alkyne (BIT-Al or PHMG-Al) in the polymer (PU-BIT or PU-PHMG) is 3.00%.

DETAILED DESCRIPTION

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 10" should be considered to include any and all subranges beginning with a minimum value of 1 or more and ending with a maximum value of 10 or less, e.g., 1 to 6, 3 to 9, or 4 to 7.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

The present disclosure provides clickable antimicrobial polymers, clickable polymers, clickable antimicrobial monomers, and functionalized antimicrobial polymers. For example, in some embodiments, clickable antimicrobial polymers described herein have one or more side-chains including an alkyne (or other clickable moiety) and a quaternary ammonium group (or other antimicrobial moiety), and clickable polymers described herein have one or more side-chains with an azide group (or other clickable moiety). Click functionalized molecules described herein, in some cases, are alkyne- or azide-functionalized molecules that also have an antimicrobial function or antimicrobial functional group. Also provided are methods of making and using such polymers and molecules.

Click chemistry, especially the copper-catalyzed 1,3-dipolar cycloaddition of azides and alkynes (CuAAC), was used to make antimicrobial polymers according to some embodiments of the instant disclosure. This reaction is regioselective, forming only 1,4-substituted products, is insensitive to oxygen, water and solvents, and can be performed at room temperature. The reaction proceeds with high yields and the reaction rate is much faster than many other crosslinking reactions. Another important aspect of the CuAAC reaction is this: the starting materials, azides and alkynes, are exceptionally stable and can be introduced into a wide range of polymer structures.

As described further herein, alkyne or azide containing monomers were introduced into polymer syntheses to create novel polymers with side-chain alkyne or azide groups. Click-functionalized molecules, such as click-functionalized specific antimicrobial or non-specific cationic molecules, were synthesized and incorporated into clickable antimicrobial or clickable polymers, which can significantly improve the antimicrobial properties of the clickable antimicrobial polymers or introduce the antimicrobial properties to the clickable polymers. Additionally, using the click-functionalized monomers to react with corresponding clickable polymers can confer various functions to polymers such as specific antimicrobial or non-specific antimicrobial properties.

The synthesis of clickable waterborne polymers of the disclosure, in some embodiments, was achieved through introducing small molecular clickable monomers with alkyne or azide groups into polymer backbones by step-growth polymerization to produce clickable antimicrobial polymers with one or more side-chain alkyne groups or one or more side-chain azide groups. These "clickable" polymers can link or click with click-functionalized molecules using click chemistry.

In an aspect, the present disclosure provides monomers comprising an alkyne and quaternary ammonium group or monomers comprising azide groups. The monomers can be used to synthesize clickable polymers.

Figure 10:
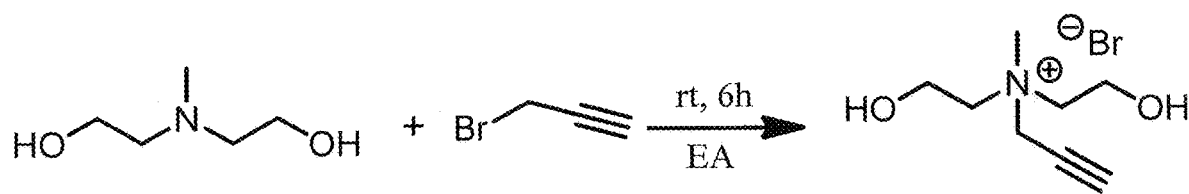
FIG. 10 illustrates the synthesis of a clickable diol with a quaternary ammonium group and clickable functional group (M1), which are suitable for preparing clickable antimicrobial polymers via step-growth polymerization. This figure is consistent with the embodiment of Example 1.
Figure 11A:
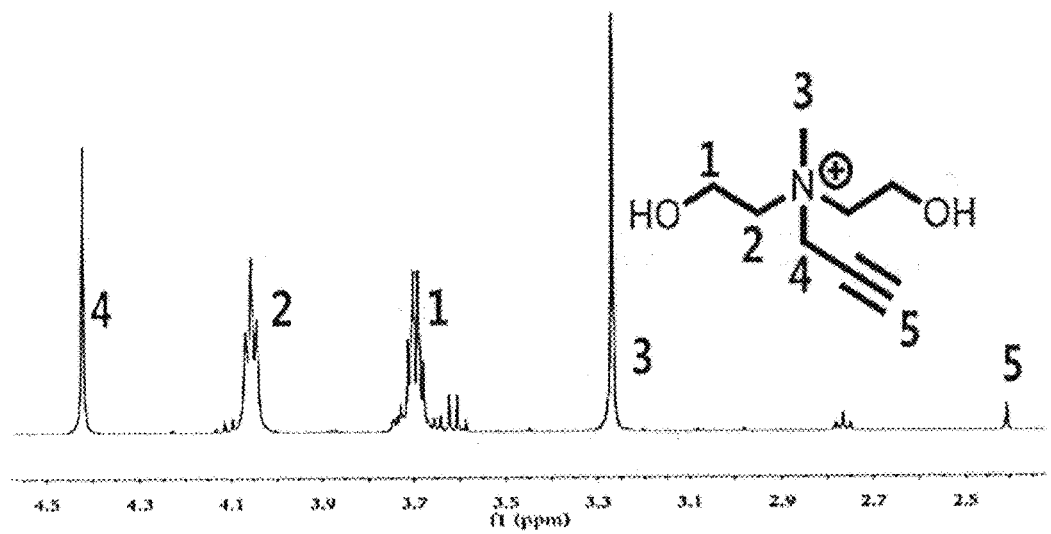
FIGS. 11A-D illustrate the Fourier Transform Infrared (FTIR) spectra and proton nuclear magnetic resonance ($^1$H NMR) spectra of the clickable diol with a quaternary ammonium group and a clickable functional group synthesized in Example 1, and of the clickable small molecule having an azide group synthesized in Example 4. The successful synthesis of clickable diols with quaternary ammonium group and clickable functional group was verified by the $^1$H NMR peaks of protons on OH—CH$_2$— (δ 3.72 ppm, m), —CH$_2$—CH$_2$—N$^+$— (δ 4.06 ppm, t), —N$^+$—CH$_3$— (δ 3.27 ppm, s), CH$_2$—C≡CH (δ 4.42 ppm, s) and —C≡CH (δ 2.41 ppm, s) in FIG. 11A, and the characteristic infrared absorption peak at around 3312 cm$^{-1}$ for "free" hydroxyl, at 2945 cm$^{-1}$ for the CH$_2$ stretching peak and at 2121 cm$^{-1}$ for alkyne (FIG. 11B). The successful synthesis of a clickable small molecule with azide groups was confirmed by the $^1$H NMR peaks of protons on N$_3$—CH$_2$— (δ 3.31 ppm, t), —CH$_2$—N— (δ 2.46 ppm, t) and —N—CH$_3$ (δ 2.23 ppm, s) in FIG. 11C, and the characteristic infrared absorption peak at around 2108 cm$^{-1}$ for —N$_3$ and at 2779 cm$^{-1}$, 2821 cm$^{-1}$ for the N(CH$_3$)$_2$ in FIG. 11D.
Figure 11C:
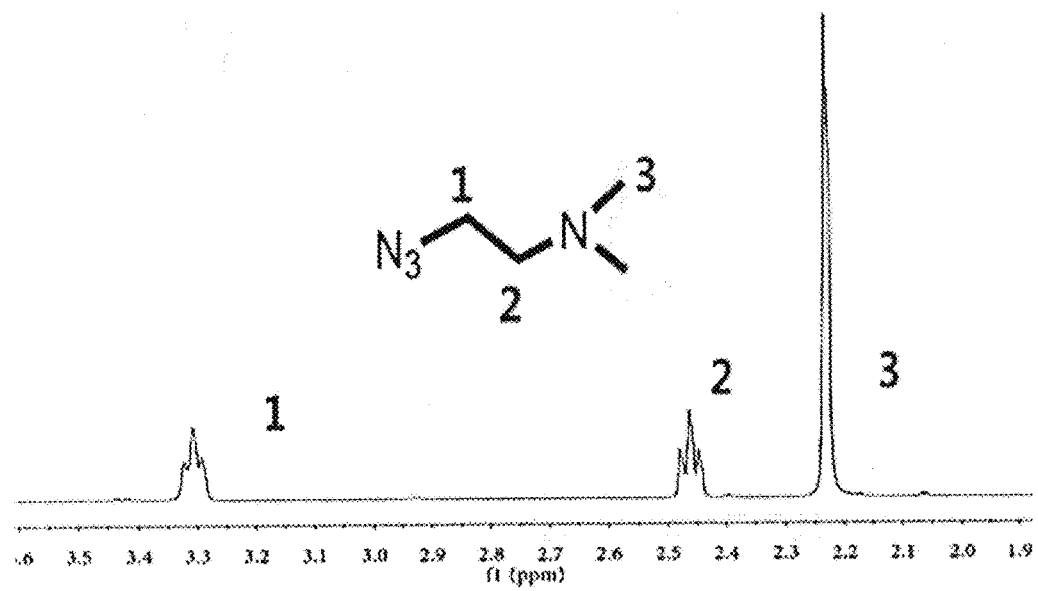
Figure 11B:
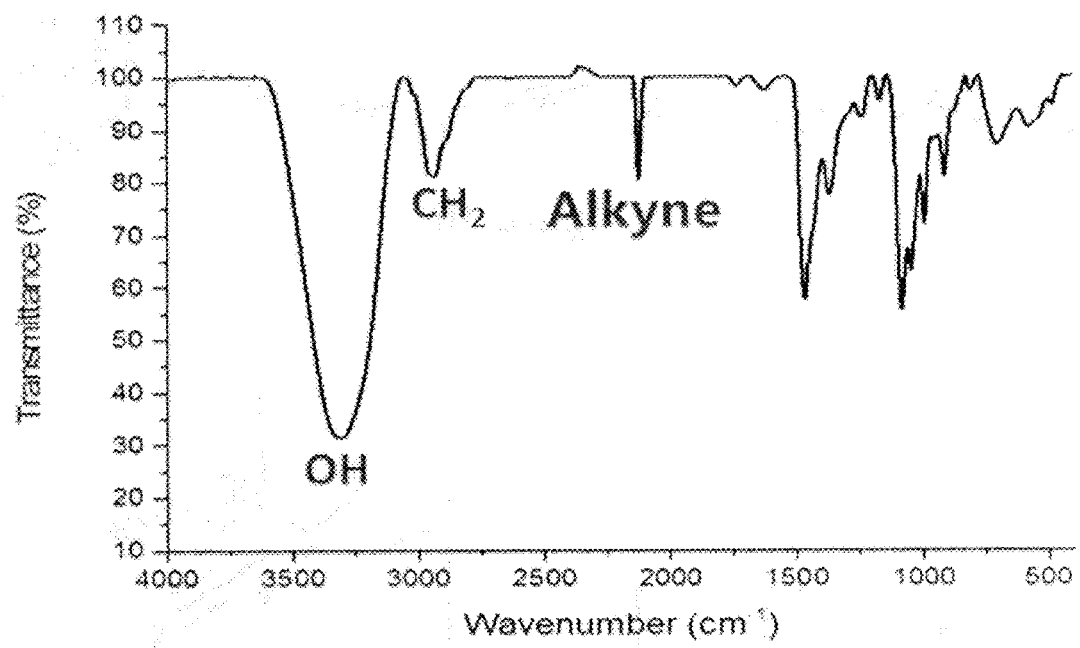
Figure 11D:
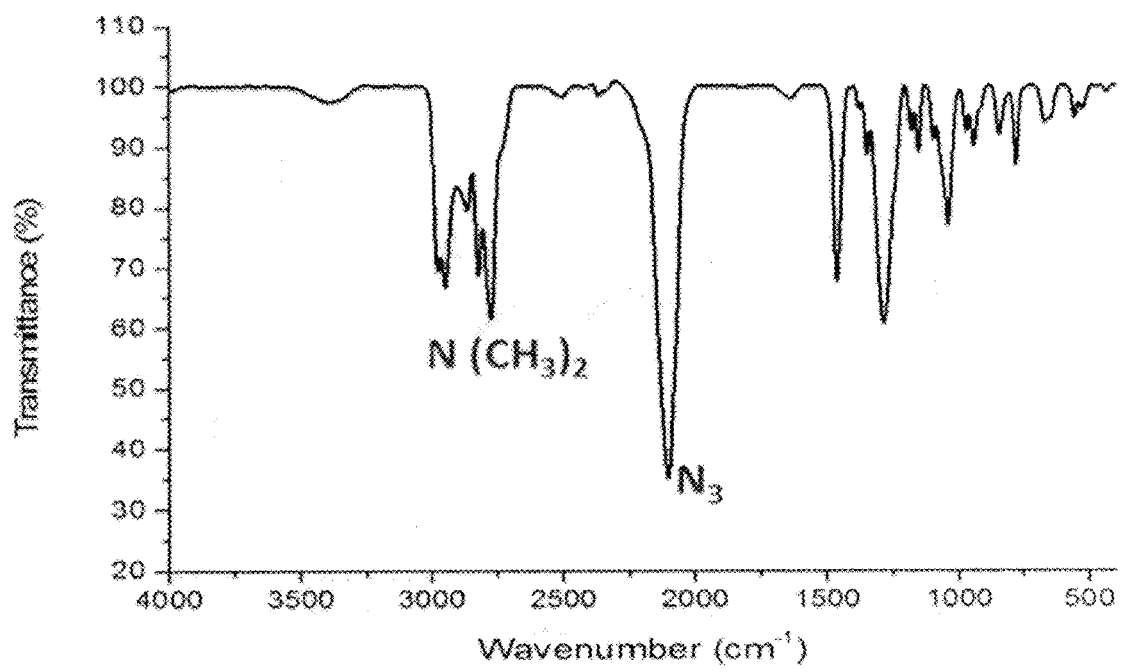
Figures 12B, 12D:
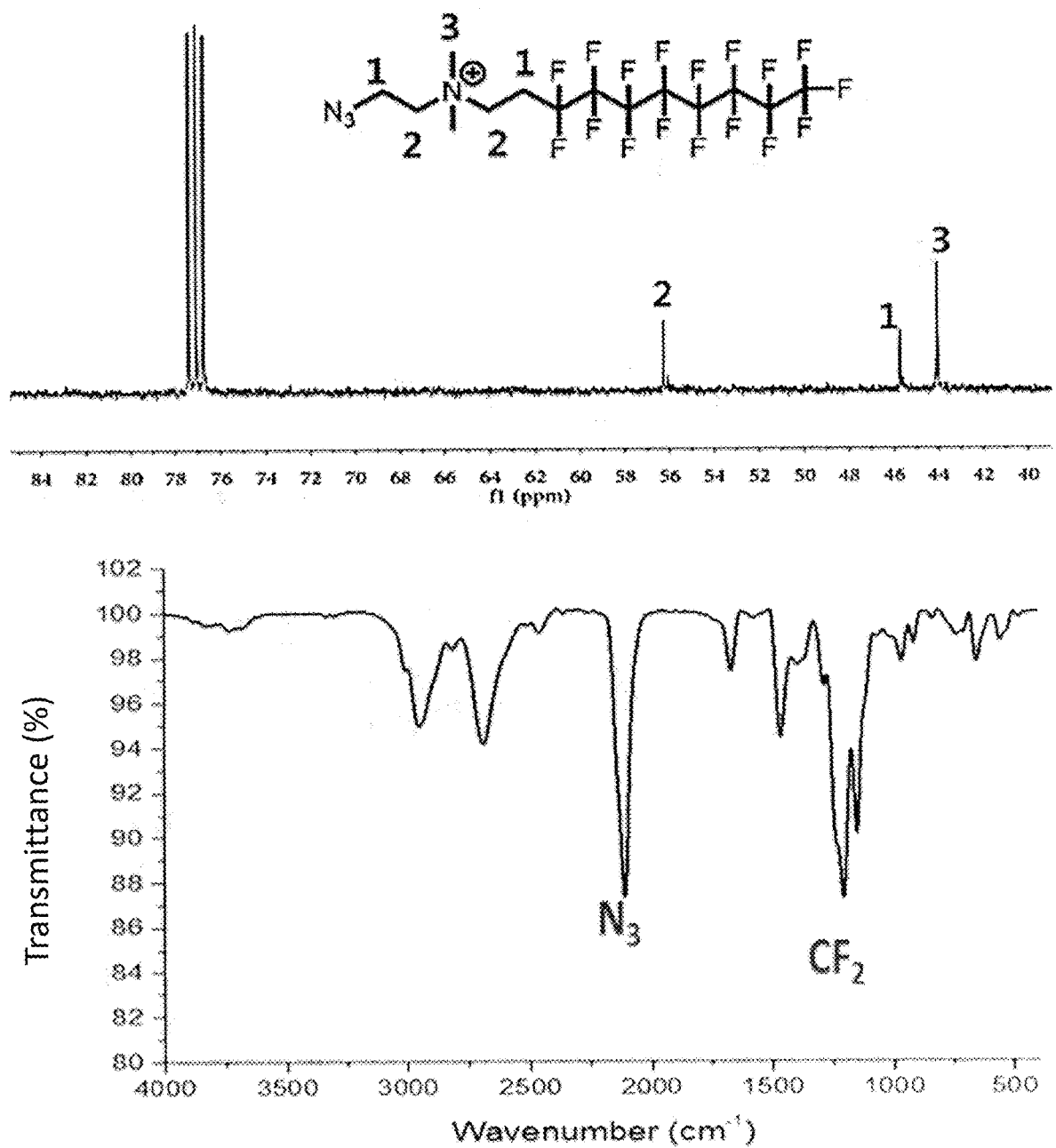
Figure 13:
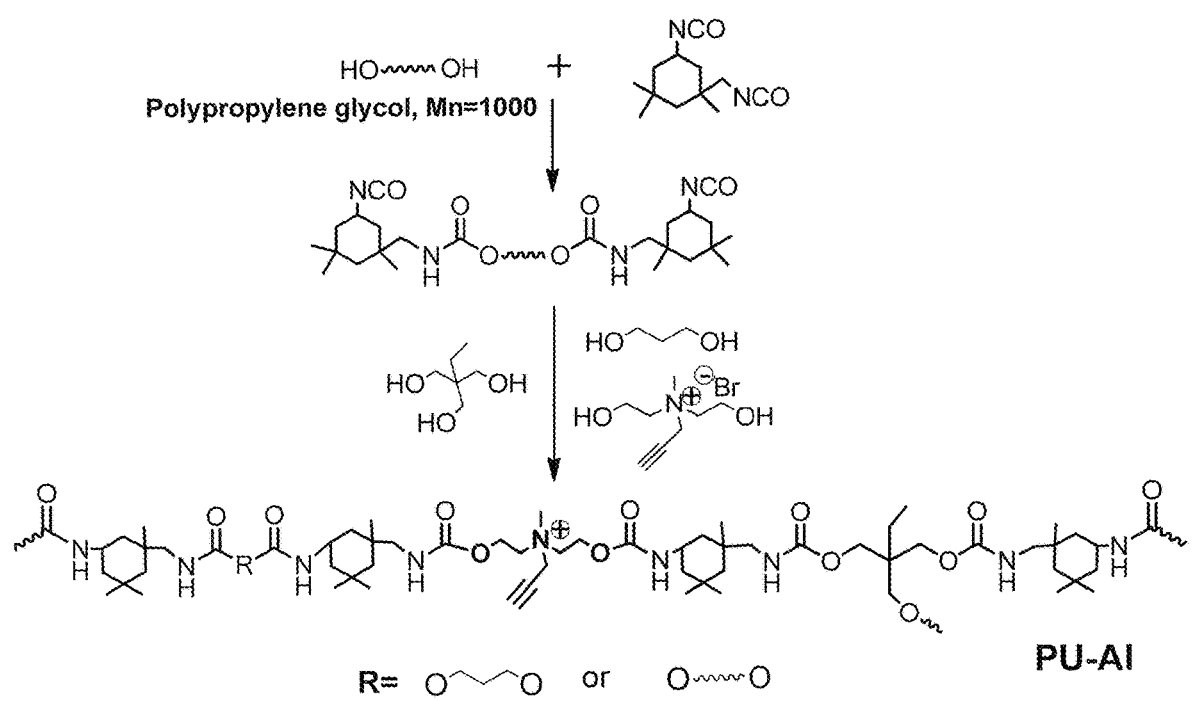
FIG. 13 shows the synthesis of clickable polyurethane with quaternary ammonium group and side-chain alkyne (PU-Al). This figure is consistent with the embodiment of Example 2.

For example, FIG. 10 illustrates a method for making small molecular clickable diols with alkyne groups which are suitable for being introduced into polymers backbone by step-growth polymerization. For example, the clickable diols can be used to produce clickable polyurethanes having one or more side-chain alkyne groups and quaternary ammonium groups.

In one embodiment, monomers described herein are clickable diols having alkyne groups in accordance with the structure of Formula M1:

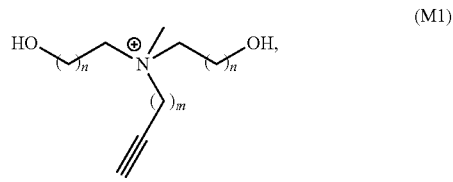

(M1)

wherein n and m are each integers from 1 to 10. In some cases, the methyl substituent on the nitrogen is replaced with a more general "R" group, which may be H or a C1-C6 hydrocarbyl group, such as $CH_3$ or $CH_2CH_3$. Such a species can be referred to as Formula M1-2.

In one aspect, the present disclosure provides clickable antimicrobial polymers. In some cases, the clickable antimicrobial polymers have at least one pendant group (i.e., a side-chain group) comprising an alkyne group. Moreover, in some embodiments, such a clickable antimicrobial polymer is made by a method disclosed herein.

In some instances, a "clickable antimicrobial polymer" is a polymer containing at least one side-chain alkyne group (or other clickable group) and at least one quaternary ammonium group (or other antimicrobial moiety). As described further herein, the antimicrobial polymers can be synthesized by step-growth polymerization. The disclosure, in some cases, provides antimicrobial polymers with side-chain alkyne groups, which are expressed by schematically in the structures of FIG. 10.

In an embodiment, the clickable antimicrobial polymer is a polyurethane polymer having at least one pendant group comprising an alkyne group. In some such instances, the amount of clickable diols (having alkyne groups) used to form the antimicrobial polyurethane was 1% to 25% by weight, based on the total weight of the polyurethane. An exemplary clickable, water dispersible polymer with side-chain alkyne groups is the clickable antimicrobial polyurethane with alkyne groups illustrated in FIG. 11.

In an aspect, the present disclosure provides methods of making clickable antimicrobial polymers. For example, the methods use the click functionalized monomers described herein (e.g., a click functional monomer containing a quaternary ammonium group) in step-growth polymerization. For example, in one embodiment, clickable antimicrobial polyurethanes with alkyne groups are synthesized by step-growth polymerization comprising (a) reacting (i) diisocyanate with (ii) polymeric polyol, at for example 70-90° C., and then (b) adding solvent (e.g., DMF), (iii) optionally a chain extender (e.g., 1,4-butanediol (BDO)), (iv) optionally a crosslinker such as trimethylolpropane (TMP)) and (v) clickable diol (e.g., having an alkyne group or other clickable moiety, and optionally also having a quaternary ammonium group or other antimicrobial moiety) to the product from (a). In this manner, clickable reactive groups and optionally quaternary ammonium groups or other antimicrobial groups can be introduced into a polymer.

Figure 1:
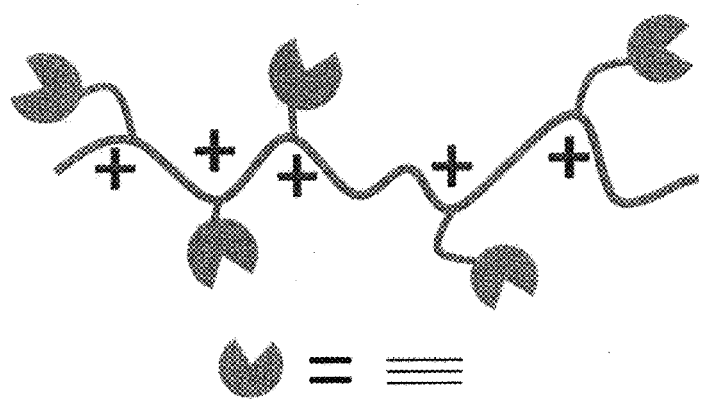
FIG. 1 schematically illustrates the structure of a clickable antimicrobial polymer according to some embodiments described herein.
Figure 2:
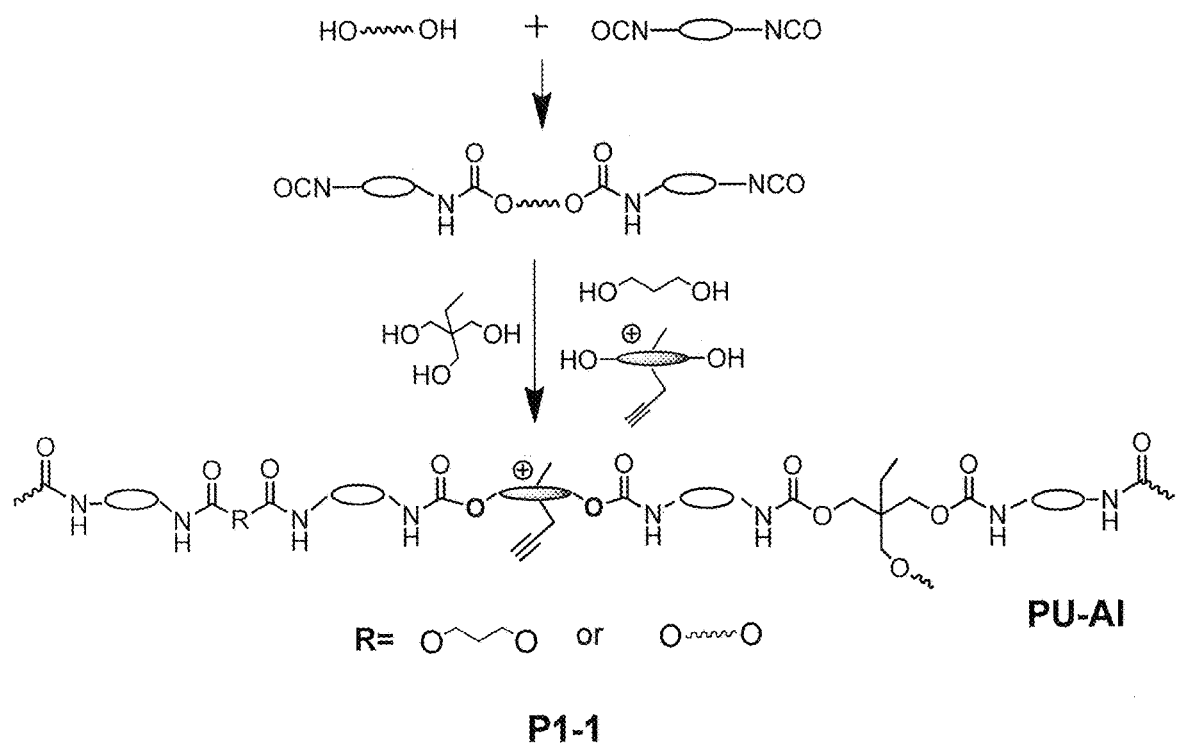
FIG. 2 illustrates a reaction scheme for synthesizing clickable antimicrobial polymers according to some embodiments described herein.

For instance, a clickable polyurethane with alkyne groups (or other clickable groups) can be synthesized by step-growth polymerization according to the scheme illustrated in FIG. 2. According to FIG. 2, the antimicrobial polyurethane with alkyne groups are prepared, for example, firstly by reacting (e.g., at 70-90° C.) (i) a diisocyanate with (ii) a polymeric polyol, then adding a solvent (such as DMF), (iii) a chain extender such as 1,4-butanediol (BDO), (iv) a crosslinker such as trimethylolpropane (TMP), and (v) a clickable diol (e.g., having an alkyne group or other clickable group, and optionally also a quaternary ammonium group or other antimicrobial group) are added to the reaction product of (i) and (ii) to introduce clickable reactive and quaternary ammonium groups into the polymer.

Examples of suitable diisocyanates that can be used to form a polymer or oligomer described herein include but are not limited to 1,6-hexamethylene diisocyanate (HDI), isophoronediisocyanate (IPDI), mixtures of 2,4- and 2,6-toluene diisocyanate (TDI), 4,4'-diphenylmethane diisocyanate (MDI), dicyclohexylmethanediisocyanate ($H_{12}$MDI), 4,4'-dibenzyl-diisocyanate, and 1,4-cyclohexylene diisocyanate. Some preferred diisocyanates are 1,6-hexamethylene diisocyanate (HDI) and isophoronediisocyanate (IPDI).

Any amount of diisocyanate not inconsistent with the objectives of the present disclosure may be used. In some cases, the amount of diisocyanate used is 15% to 65% by weight, based on the total weight of the polyurethane solid. Preferably, the amount of diisocyanate used is 25% to 55% by weight, based on the total weight of the resulting polyurethane solid.

Examples of polymeric polyols include polyethylene glycol, polypropylene glycol, polytetramethylene ether glycol, poly(butanediol-co-adipate) glycol, and polycaprolactone glycol. It is preferred to use difunctional compounds, although small amounts of trifunctional compounds may be used. Moreover, in some cases, the weight average molecular weight of the polymeric polyol is 600 to 3000. Preferably, the molecular weight of the polymeric polyol used to form a composition described herein is 1000 to 2000.

Any amount of polymeric polyol not inconsistent with the objectives of the present disclosure may be used. In some cases, the amount of polymeric polyol used is 15% to 55% by weight, based on the total weight of the polyurethane solid. Preferably, the amount of polymeric polyol used is 15% to 45% by weight, based on the total weight of the resulting polyurethane solid.

Figure 14:
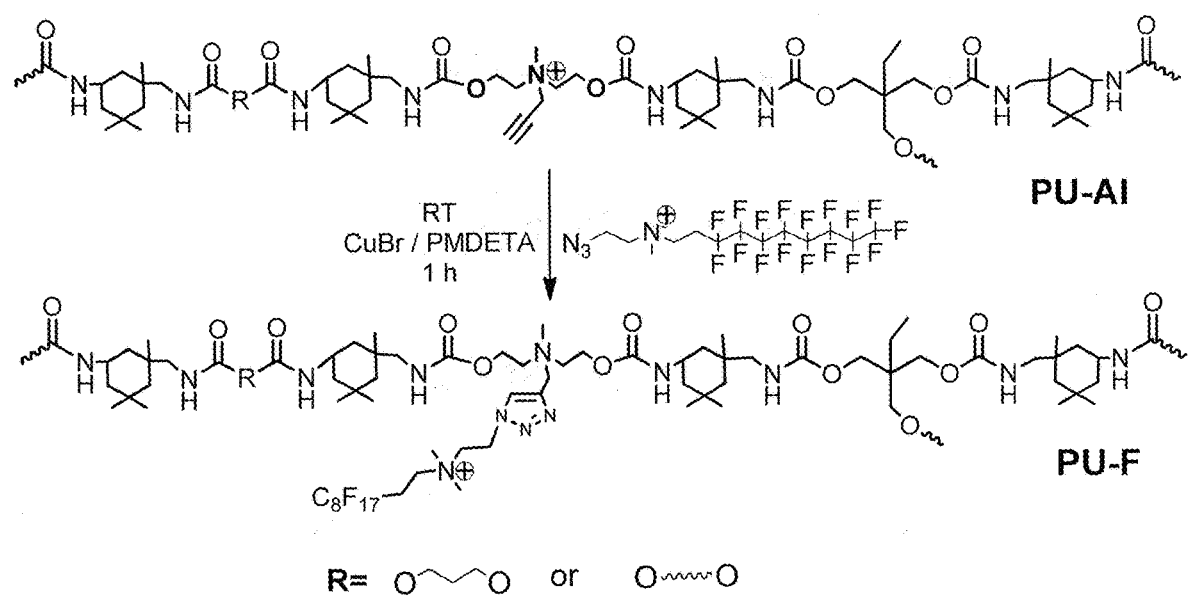
FIG. 14 shows the synthesis of polyurethane with quaternary ammonium group and fluorine (PU-F). This figure is consistent with the embodiment of Example 9.
Figure 15:
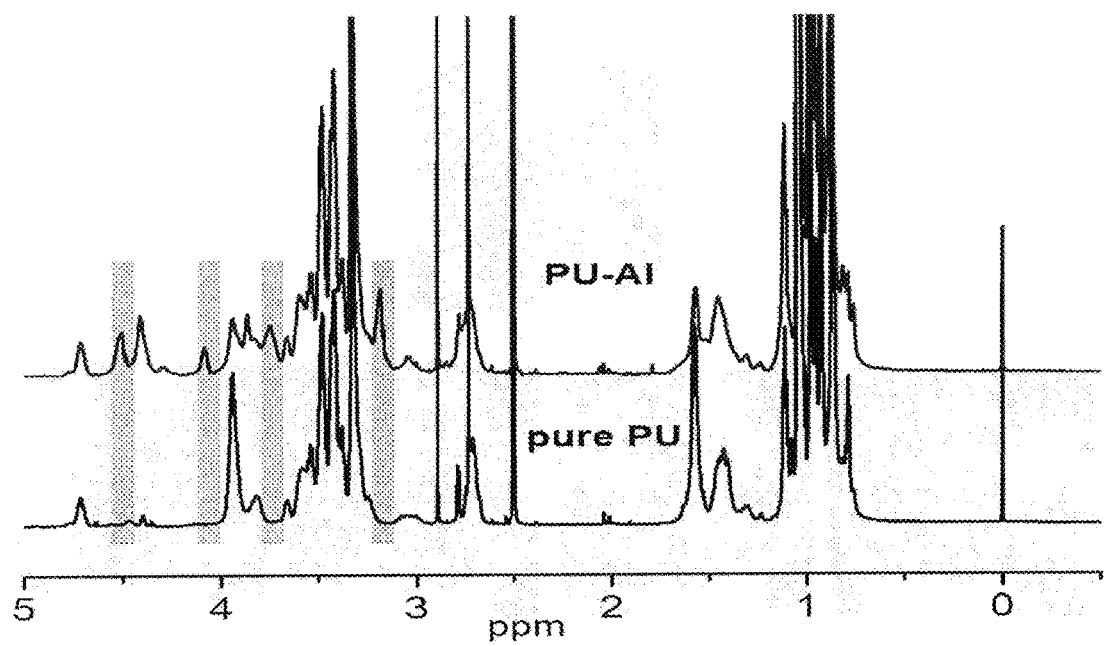
FIG. 15 shows $^1$H NMR spectra of non-clickable polyurethane (PU), and clickable polyurethane with side-chain alkyne (PU-Al), which are described in Example 2. The successful introduction of alkyne groups into polyurethanes was indicated by the appearance of the proton peaks of —N$^+$(CH$_3$)—CH$_2$—C≡CH (δ 3.18 ppm), —N$^+$CH$_2$—CH$_2$—OH (δ 3.74 ppm), —N$^+$CH$_2$—CH$_2$—OH (δ 4.08 ppm), and —N$^+$—CH$_2$—C≡CH (δ 4.51 ppm) in the $^1$H NMR spectrum.
Figure 16:
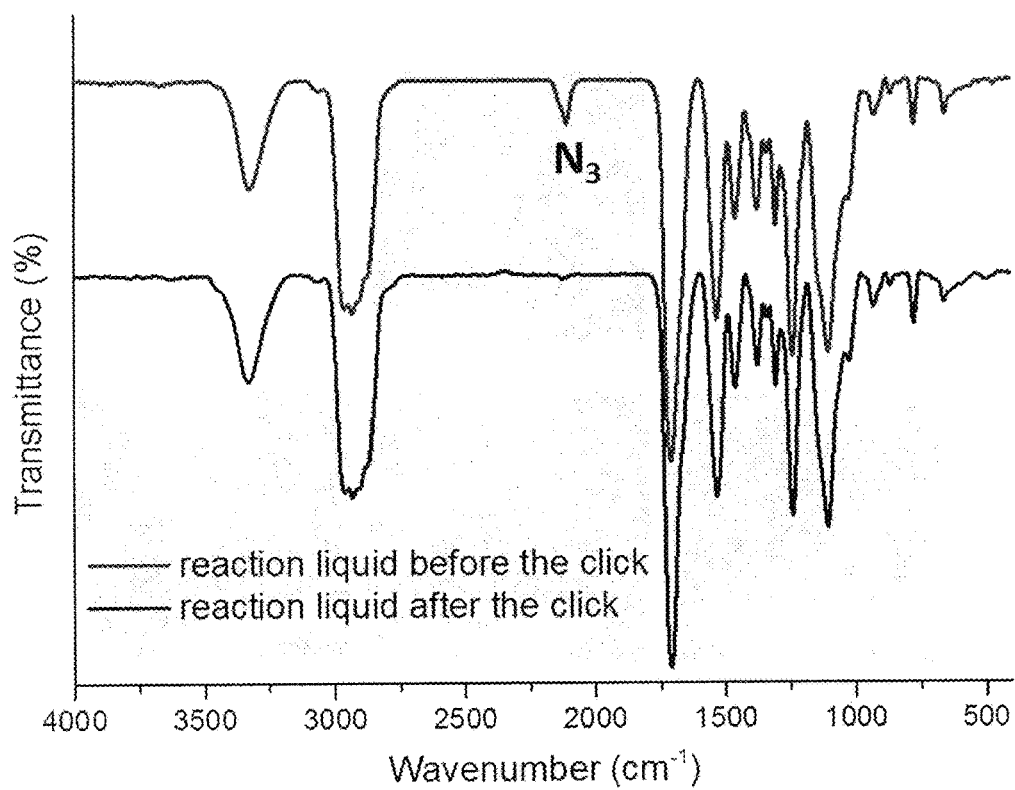
FIG. 16 shows the FTIR spectra of the reaction liquid whose solvent was evaporated by infrared lamp, as described in Example 9. After applying the copper(I)-catalyzed alkyne-azide cycloaddition (CuAAC, click reaction), the azide groups were consumed by the click reaction, as indicated by the disappearance of the characteristic infrared peak of azide group at 2106 cm$^{-1}$ of the clickable small molecules with quaternary ammonium group and fluorine.
Figure 17:
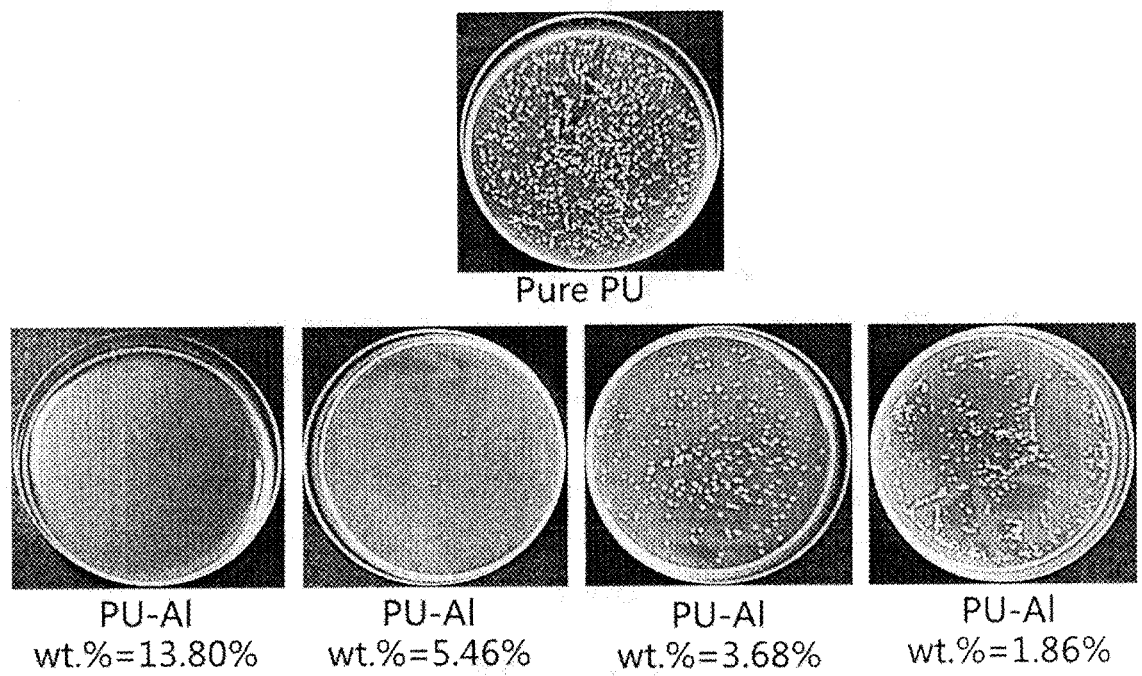
FIG. 17 shows antibacterial activity of clickable polyurethane with quaternary ammonium group and side-chain alkyne (PU-Al) against *Staphylococcus aureus*. According to the results, PU-Al presents an excellent antimicrobial property, antibacterial rate above 99% against the *Staphylococcus aureus*, when the mass percent of clickable diol with quaternary ammonium group and clickable functional group (M1) in the polymer (PU-Al) is 5.46%. However, antibacterial rate of PU-Al is about 70% when the mass percent of M1 in the polymer (PU-Al) is 3.68%.
Figure 18:
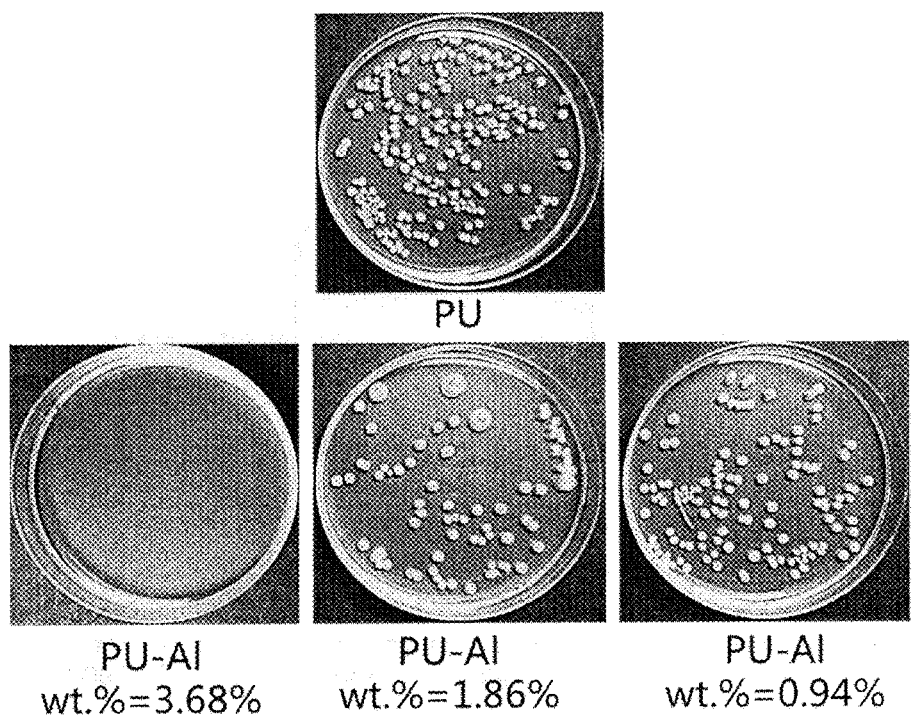
FIG. 18 shows antibacterial activity of clickable polyurethane with quaternary ammonium group and side-chain alkyne (PU-Al) against *Escherichia coli*. According to the results, PU-Al kills all the *Escherichia coli* when the mass percent of clickable diol with quaternary ammonium group and clickable functional group (M1) in the polymer (PU-Al) is 3.68%. Antibacterial rate of PU-Al is about 62% when the mass percent of M1 in the polymer (PU-Al) is down to 1.84%.
Figure 19:
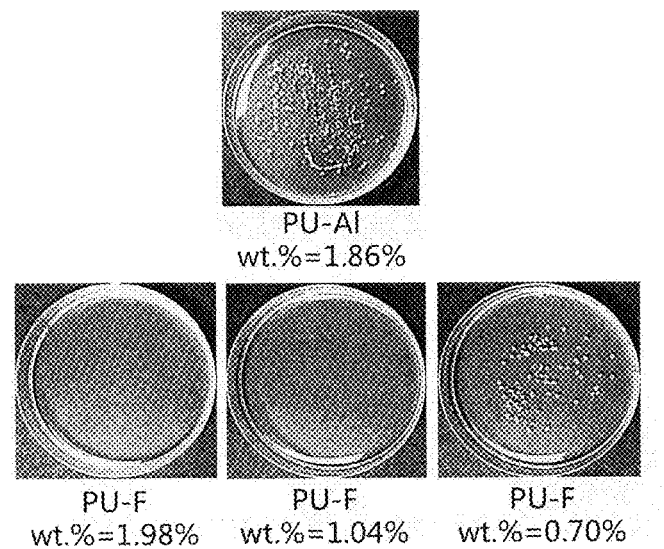
FIG. 19 shows antibacterial activity of polyurethane with quaternary ammonium group and fluorine (PU-F) against the *Staphylococcus aureus*, which is synthesized from PU-Al (wt. %=1.86%). According to the results, PU-F killed all the *Staphylococcus aureus* when the mass percent of clickable small molecule with quaternary ammonium group and fluorine in the polymer (PU-F) is 1.04%. Antibacterial rate of PU-F is about 58% when the mass percent of clickable small molecule in the polymer (PU-F) is 0.70%.
Figure 20:
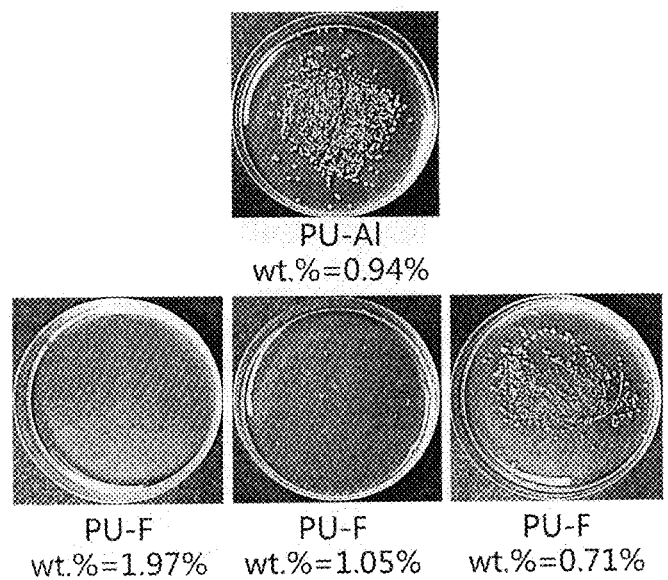
FIG. 20 shows antibacterial activity of polyurethane with quaternary ammonium group and fluorine (PU-F) against the *Staphylococcus aureus*, which is synthesized from PU-Al (wt. %=0.94%). According to the results, PU-F presents an excellent antimicrobial property, with an antibacterial rate above 99% against the *Staphylococcus aureus*, when the mass percent of clickable small molecule with quaternary ammonium group and fluorine in the polymer (PU-F) is 1.05%. Antibacterial rate of PU-F is about 50% when the mass percent of clickable small molecule in the polymer (PU-F) is 0.71%.
Figure 21:
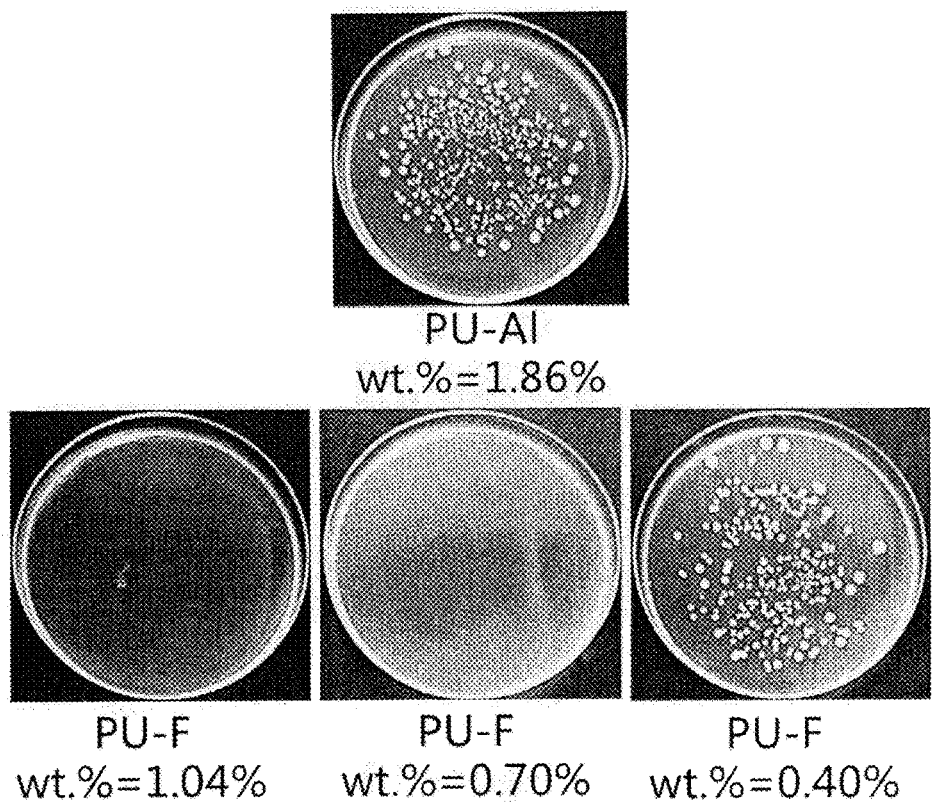
FIG. 21 shows antibacterial activity of polyurethane with quaternary ammonium group and fluorine (PU-F) against the *Escherichia coli*, which is synthesized from PU-Al (wt. %=1.84%). According to the results, PU-F killed all the *Escherichia coli* when the mass percent of clickable small molecule with quaternary ammonium group and fluorine in the polymer (PU-F) is 0.70%. Antibacterial rate of PU-F is about 28% when the mass percent of clickable small molecule in the polymer (PU-F) is 0.40%.
Figure 22:
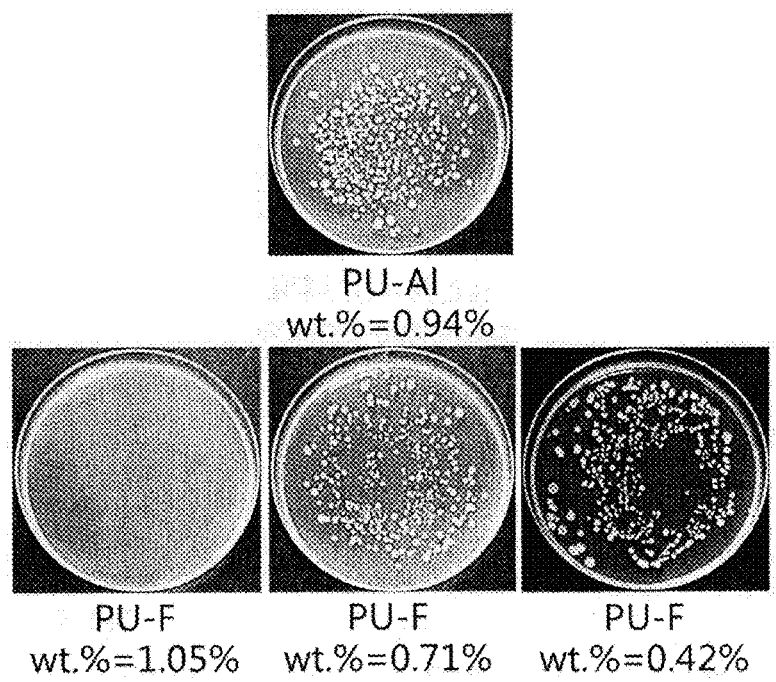

With regard to the preparation of antimicrobial polyurethane with alkyne groups (e.g., (FIG. 14)), clickable diols with alkyne groups include, for example, M1 or M1-2. Any amount of such a clickable diol monomer not inconsistent with the objectives of the present disclosure may be used. In some cases, the amount of clickable diol monomer (e.g., with alkyne groups) is 1% to 25% by weight, based on the total weight of the polyurethane solid.

In another aspect, the present disclosure provides clickable polymers. In some cases, the clickable polymers have has at least one pendant group (i.e., a side-chain group) comprising an azide group. In some embodiments, a clickable polymer is made by a method disclosed herein.

Figure 3:
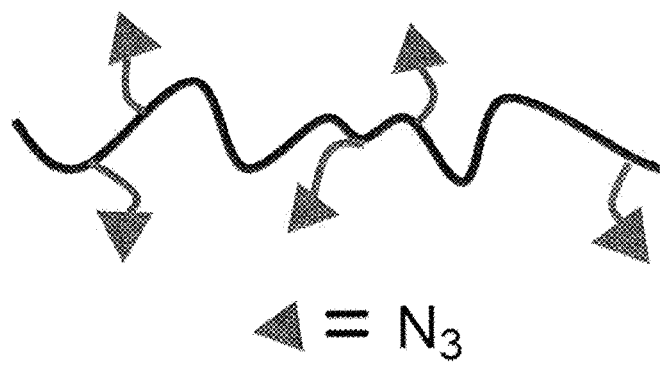
FIG. 3 schematically illustrates the structure of a clickable antimicrobial polymer according to some embodiments described herein.

A "clickable polymer," in some cases, refers to a polymer containing at least one side-chain azide group (or other clickable group) and at least one quaternary ammonium group (or other antimicrobial group). The antimicrobial polymers can be synthesized by step-growth polymerization. The disclosure provides polymers with side-chain azide groups, which are illustrated schematically in FIG. 3.

Figure 4:
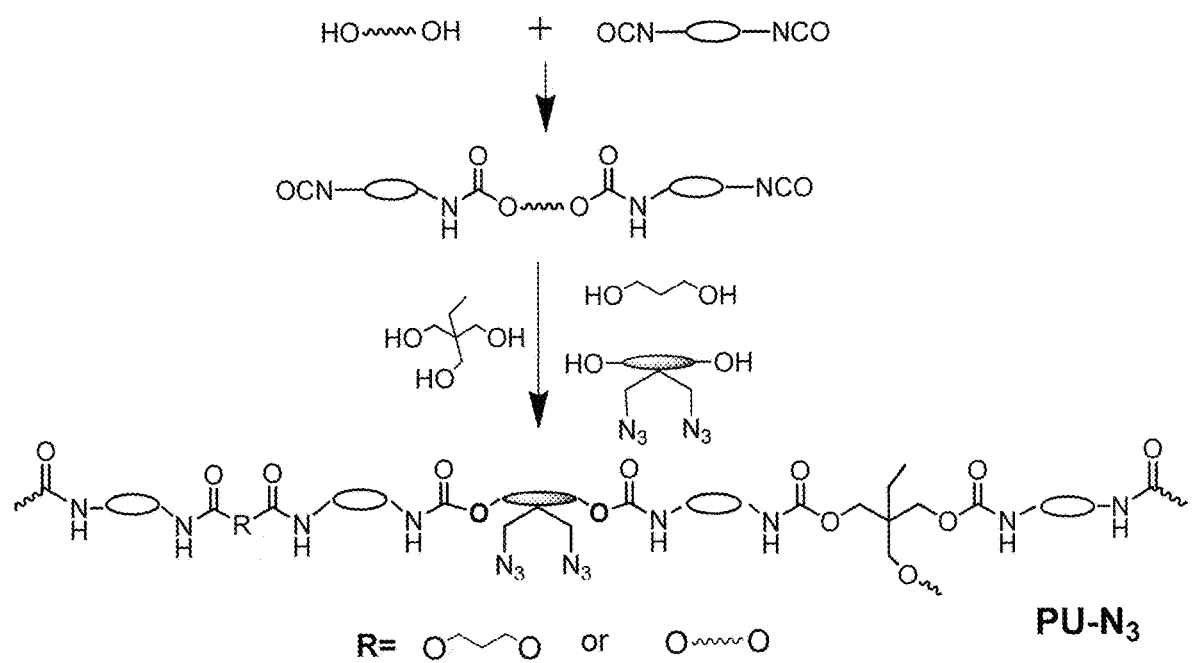
FIG. 4 illustrates a reaction scheme for synthesizing clickable antimicrobial polymers according to some embodiments described herein.

In one embodiment, the clickable polymer is a polyurethane polymer having at least one pendant group comprising an azide group. Any amount of clickable diol not inconsistent with the objectives of the present disclosure may be used to form such a polyurethane. In some cases, the amount of clickable diol (with azide groups) is 5% to 25% by weight, based on the total weight of the polyurethane. FIG. 4 illustrates an exemplary synthetic scheme for forming a clickable polymer described herein. In FIG. 4 (as in other figures), the ovals represent other portions of the monomers or polymers, such as portions of a monomer or polymer including an antimicrobial moiety, such as a quaternary ammonium moiety.

Methods of making clickable polymers are also described herein. In some embodiments, clickable polyurethanes with azide groups are synthesized by step-growth polymerization, the method more particularly comprising (a) reacting (i) one or more diisocyanates with (ii) one or more polymeric polyols (at 70-90° C., for example), and then (b) adding solvent (e.g., DMF), (iii) optionally a chain extender (e.g., BDO)), (iv) optionally a crosslinker such as trimethylolpropane (TMP), and (v) one or more clickable diols having an azide group (or other clickable moiety) to the product from (a). In this manner, clickable reactive groups can be introduced into the polymer.

For example, clickable polyurethane with azide groups can be synthesized by step-growth polymerization according to the scheme illustrated in FIG. 4. According to the scheme of FIG. 4, polyurethane with azide groups is prepared, for example, by reacting (i) diisocyanate with (ii) polymeric polyol. Next, DMF, (iii) BDO, (iv) trimethylolpropane (TMP), and (v) clickable diol with azide group are added to introduce clickable reactive groups.

Examples of suitable diisocyanates for use in such a scheme include those include those mentioned above, such as HDI and IPDI. Any amount of diisocyanate not inconsistent with the objectives of the present disclosure may be used. In some cases, the amount of diisocyanate is 25% to 65% by weight, based on the total weight of the polyurethane solid. Preferably, the amount of diisocyanate is 25% to 55% by weight, based on the total weight of the polyurethane solid.

Examples of polymeric polyol for use in a scheme such as that of FIG. 4 include all of those polyols mentioned above, such as polyethylene glycol, polypropylene glycol, polytetramethylene ether glycol, poly(butanediol-co-adipate) glycol, and polycaprolactone glycol. It is preferred to use difunctional compounds (diols), although small amounts of trifunctional compounds (triols) may be used. In some cases, the weight average molecular weight of the polymeric polyol is 600 to 3000 or 1000 to 2000. Any amount of polyol not inconsistent with the objectives of the present disclosure may be used. For example, in some embodiments, the amount of polymeric polyol is 15-55% or 15-45% by weight, based on the total weight of the polyurethane solid.

With regard to the preparation of polyurethane with azide groups (e.g., (FIG. 4)), clickable diols with azide groups include, for example, M2 (described further below). Any amount of clickable diol not inconsistent with the objectives of the present disclosure may be used. For instance, in some cases, the amount of clickable diols with azide groups is 1% to 25% by weight, based on the total weight of polyurethane solid.

Figure 5:
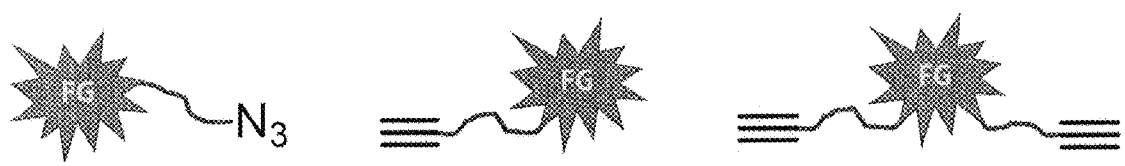
FIG. 5 schematically illustrates the structures of click-functionalized molecules according to some embodiments described herein.

In still another aspect, the present disclosure provides click-functional or—functionalized molecules or monomers comprising one or two alkynes or azides. Such click-functionalized molecules may also exhibit antimicrobial behavior. In some cases, such click-functionalized molecules can be synthesized via the clickable modification of functional molecules with, for example, an antimicrobial functional group. A "functional" molecule refers to a molecule having a function or functional group (e.g., an antimicrobial group) other than the clickable function or functional group(s). The structures of exemplary species are illustrated schematically in FIG. 5. In FIG. 5, the clickable groups include an alkyne group and/or an azide group. The other functional group (such as the antimicrobial functional group) is illustrated schematically as "FG" in FIG. 5.

In some embodiments, the functional molecules are molecules containing fluorine and quaternary ammonium with antimicrobial function, which can improve the antimicrobial properties of coatings and films via antimicrobial molecules containing fluorine presented onto the material surfaces. A scheme for synthesizing an exemplary click-functionalized molecule including an azide group and fluorine functional groups is illustrated in FIG. 6.

Figure 6:
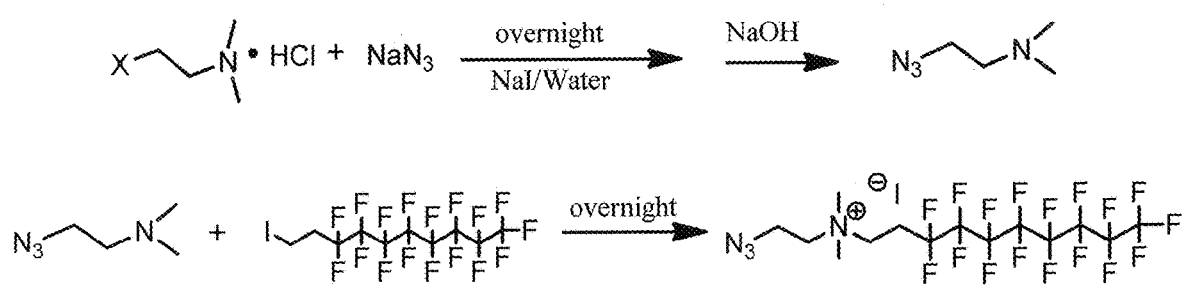
FIG. 6 schematically illustrates a reaction scheme for synthesizing an exemplary click-functionalized molecule according to one embodiment described herein. This figure is consistent with the embodiment of Example 4.

With reference to one exemplary embodiment consistent with FIG. 6, firstly, 2-azido-N,N-dimethylethanamine is prepared by reacting (i) sodium azide, (ii) a dimethylaminoethyl halogen hydrochloride, such as dimethylaminoethylchlorine hydrochloride and dimethylaminoethylbromine hydrochloride at the molar ratio of sodium azide to dimethylaminoethyl halogen as 3~1:1, in (iii) suitable solvent, such as such as methanol, ethanol, isopropanol, diethyl ether, tetrahydrofuran, DMSO and DMF, with the catalysis of (iii) sodium iodide at a temperature of 60-110° C. for 16-24 hours. Then functional molecules containing fluorine and quaternary ammonium are prepared by reacting (i) 2-azido-N,N-dimethylethanamine, (ii) halogenated hydrocarbon containing fluorine, such as 1-Iodo-1H,1H,2H,2H-perfluorodecane, perfluorodecyl bromide, 1H,1H,2H,2H-perfluorooctyl iodide and 1-bromoheptadecafluorooctane at the molar ratio of 2-azido-N,N-dimethylethanamine to halogenated hydrocarbon containing fluorine as 2-1:1, in (iii) suitable solvent, such as such as methanol, ethanol, isopropanol, diethyl ether, tetrahydrofuran, DMSO and DMF at a temperature of 40-90° C. for 16-20 hours.

Figure 7:
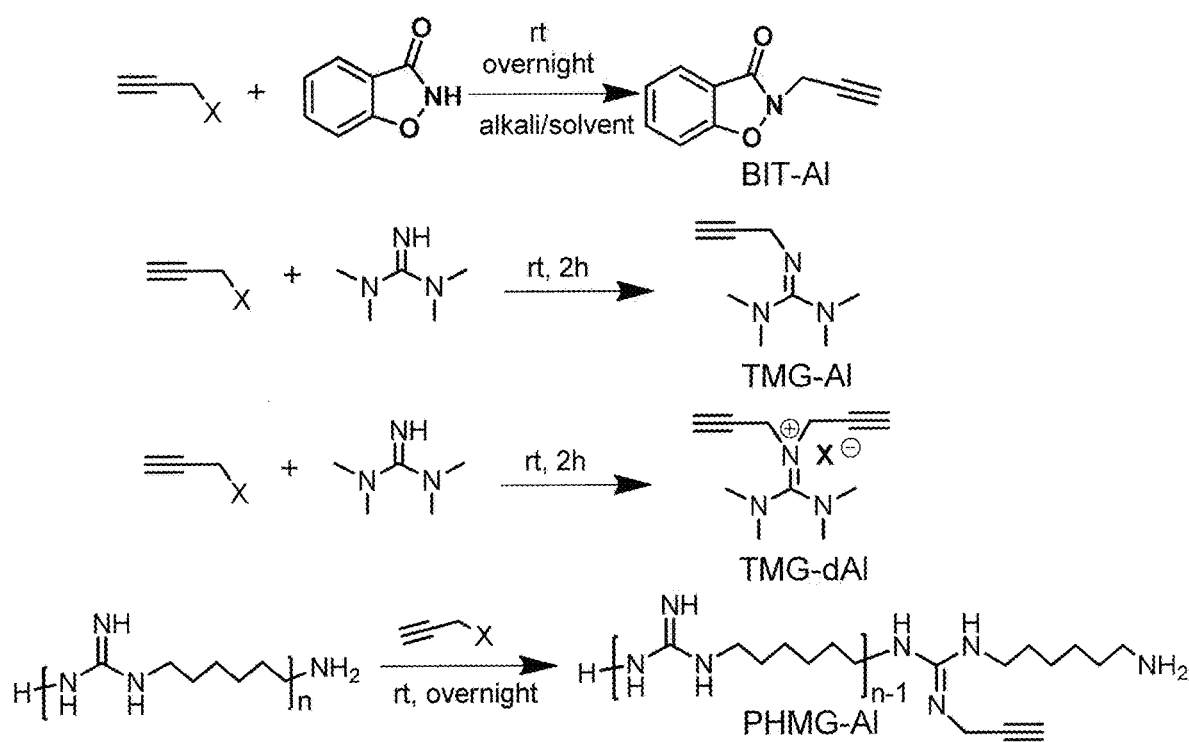
FIG. 7 schematically illustrates the structures of click-functionalized molecules according to some embodiments described herein.

For example, the functional molecules are 1,2-Benzisothiazolin-3-one (BIT) with antimicrobial function, trimethylguanidine (TMG) with antimicrobial function, and polyhexamethylene guanidine (PHMG) with antimicrobial function. Reaction schemes for preparing click-functionalized molecules including alkyne modified benzisothiazolinone (BIT-Al), alkyne modified trimethylguanidine (TMG-Al), and alkyne modified polyhexamethylene guanidine hydrochloride (PHMG-Al) are illustrated in FIG. 7.

BIT-Al is prepared by reacting (i) BIT, (ii) 3-halo-propynyl, such as 3-chloro-propynyl and 3-bromo-propynyl at a molar ratio of BIT to 3-halo-propynyl as 1:1.1-2.0, in (iii) suitable solvent, such as such as methanol, ethanol, isopropanol, diethyl ether, tetrahydrofuran and DMF, with the catalyst of (iv) alkali, such as sodium hydride, sodium methoxide and sodium ethoxide at a temperature of 30-50° C. for 16-24 hours.

TMG-Al is prepared by reacting (i) TMG, (ii) 3-halopropynyl, such as 3-chloro-propynyl and 3-bromo-propynyl at a molar ratio of TMG to 3-halo-propynyl as 1:1.1-2.0, in (iii) suitable solvent, such as such as methanol, ethanol, isopropanol, diethyl ether, tetrahydrofuran and DMF, with the catalyst of (iv) alkali, such as sodium hydride, sodium methoxide and sodium ethoxide at a temperature of 30-50° C. for 16-24 hours.

TMG-dAl is prepared by reacting (i) TMG, (ii) 3-halopropynyl, such as 3-chloro-propynyl and 3-bromo-propynyl, at a molar ratio of TMG to 3-halo-propynyl as 1:2.0-3.0, in (iii) suitable solvent, such as such as methanol, ethanol, isopropanol, diethyl ether, tetrahydrofuran and DMF, with the catalyst of (iv) alkali, such as sodium hydride, sodium methoxide and sodium ethoxide at a temperature of 30-50° C. for 16-24 hours.

PHMG-alkyne is prepared by reacting (i) PHMG, (ii) 3-halo-propynyl, such as 3-chloro-propynyl and 3-bromo-propynyl at the molar ratio of PHMG to 3-halo-propynyl as 1:1.1-2.0, in (iii) suitable solvent, such as such as methanol, ethanol, isopropanol, diethyl ether, tetrahydrofuran and DMF, with the catalyst of (iv) alkali, such as sodium hydride, sodium methoxide and sodium ethoxide at a temperature of 30-50° C. for 16-24 hours.

Figure 8:
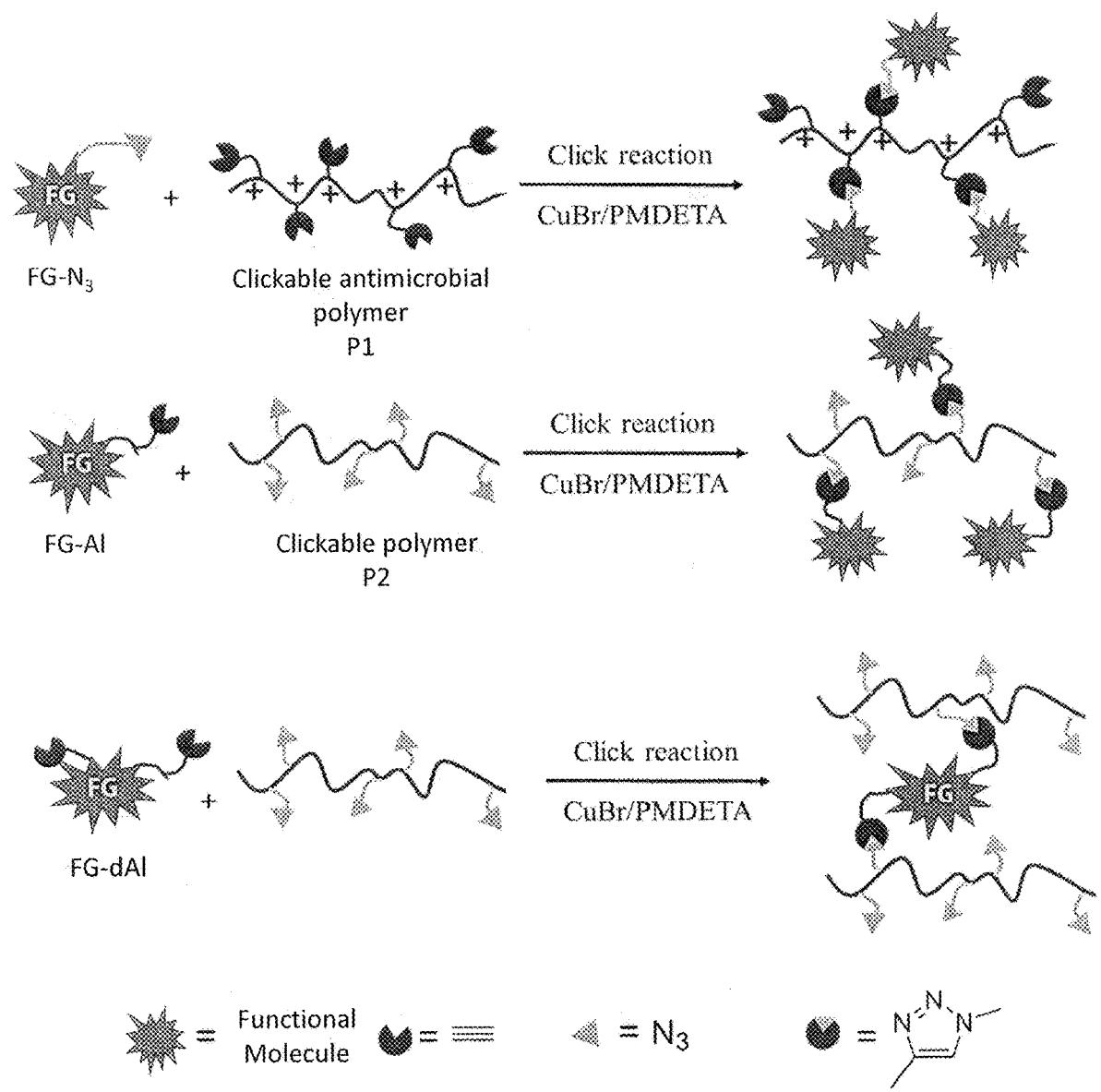
FIG. 8 schematically illustrates reaction schemes for forming compositions according to some embodiments described herein.

In still another aspect, the present disclosure provides antimicrobial polymers comprising one or more pendant functional molecules covalently bound to the polymer backbone by a linking group comprising a 1,2,3-triazole (i.e., functionalized antimicrobial polymers). Such antimicrobial polymers can be synthesized using a process of click reaction between a clickable polymer and a click-functionalized molecule, wherein a clickable polymer with side-chain alkyne (P1) or side-chain azide groups (P2) is clicked with a click-functionalized molecule with azide groups (FG-$N_3$) or alkyne groups (FG-Al) catalyzed by, for example, copper (I) bromide/copper(I)chloride and N,N,N',N'',N''-Pentamethyldiethylenetriamine (PMDETA) or $CuSO_4.5H_2O$ and sodium ascorbate. In one embodiment, the antimicrobial polymer is a polyurethane having at least one linking group, wherein the linking group comprises a 1,2,3-trazole (e.g., a 1,4-substituted 1,2,3-triazole). A click reaction via clickable polymers to functionalized molecule reaction is illustrated in the scheme of FIG. 8.

In another aspect, the present disclosure provides methods of making crosslinked antimicrobial polymers, including crosslinked antimicrobial polymers described above. For example, in some cases, the clickable antimicrobial polymers or clickable polymers are polyurethane polymers having at least one pendant group as azide group or at least one pendant group as alkyne group.

Figure 9:
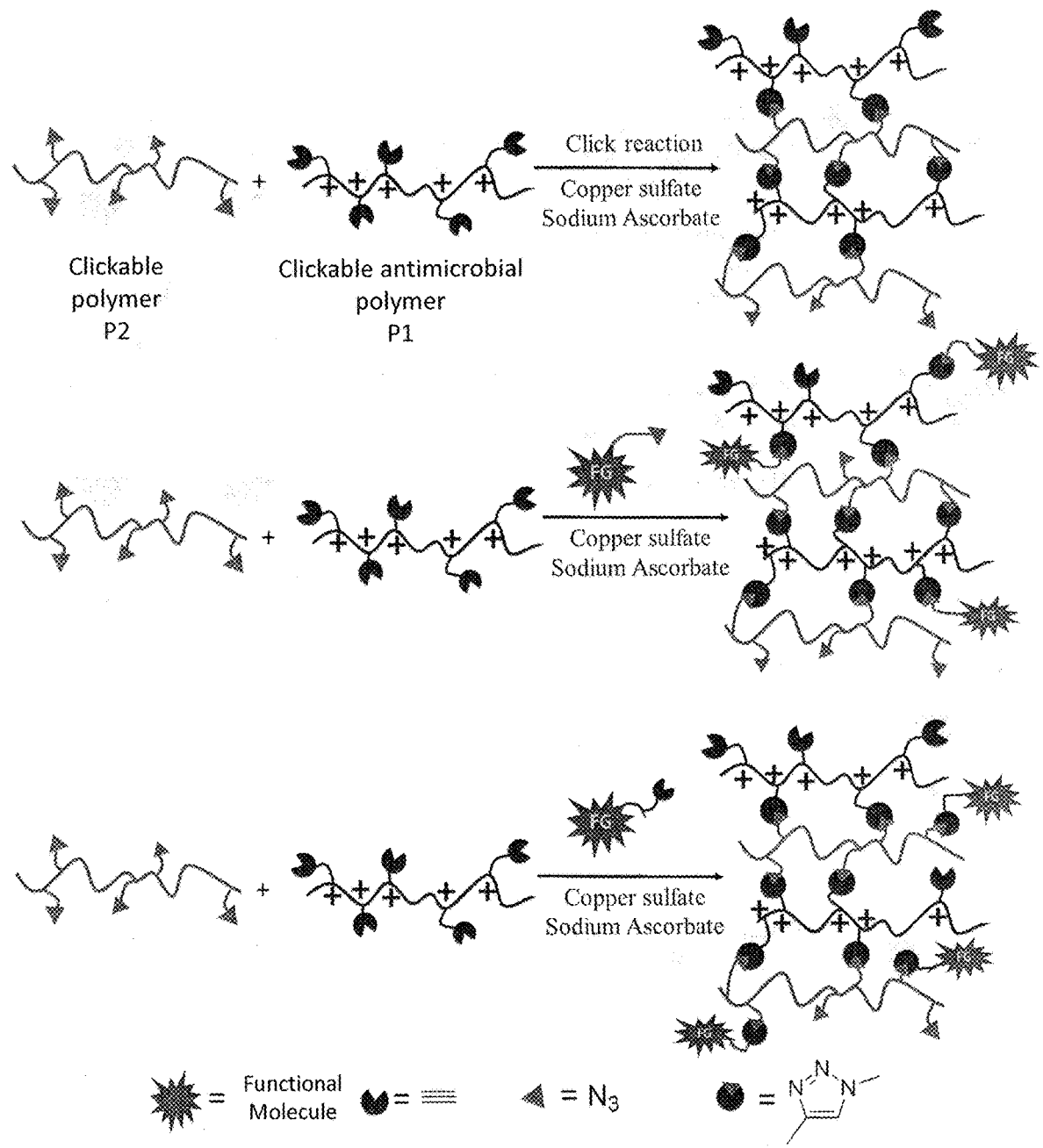
FIG. 9 schematically illustrates reaction schemes for forming compositions according to some embodiments described herein.

In one exemplary embodiment, a clickable antimicrobial polymer with side-chain alkyne groups (P1) is click-crosslinked with a corresponding clickable polymer with side-chain azide groups (P2) in the presence/absence of functional molecules with alkyne and/or azide group under catalysis, for example, copper(I) bromide/copper(I) chloride and N,N,N',N'',N''Pentamethyldiethylenetriamine (PMDETA) or $CuSO_4.5H_2O$ and sodium ascorbate catalysis. The click crosslinking via polymer to polymer and/or azide/alkyne functionalized small molecules reaction is illustrated schematically in FIG. 9.

In some cases, a method of crosslinking a clickable antimicrobial polymer/clickable polymer (e.g., a clickable antimicrobial polyurethane/clickable polyurethane) comprises crosslinking a clickable polymer having at least one pendant group including an azide group or at least one pendant group including an alkyne group and further comprising a quaternary ammonium salt group. Such crosslinking can be carried out in the presence/absence of alkyne or/and azide functionalized molecules with a copper(I)/copper (II) catalysts, for example, copper(I) bromide/copper (I) chloride and N,N,N',N'',N'' Pentamethyldiethylenetriamine (PMDETA) or $CuSO_4 \cdot 5H_2O$ and sodium ascorbate, under conditions such that a crosslinking group comprising a 1,2,3-triazole is formed. The 1,2,3-triazole(s) of the crosslinking group(s) of cross-linked polymer (e.g., a cross-linked polyurethane) is/are formed by the reaction of a pendant azide group and a pendant alkyne group. The pendant azide group and pendant alkyne group can be on the same polymer chain or different polymer chains.

In still another aspect, the present disclosure provides uses of small molecules, monomers, polymers or oligomers, and/or compositions described herein. For example, in some cases, a polymer or composition described herein is used in a coating or film, or as a coating or film of a surface. Examples of such coatings and adhesives include, but are not limited to, exterior and interior coatings, coil coatings, marine coatings, leather coatings, wood coatings, textile coatings, plastic coatings, metal anticorrosive coatings and shoe coatings and films.

Some embodiments described herein are further illustrated in the following non-limiting Examples.

Example 1

Example of Synthesis of Clickable Diols with Alkyne Groups (M1, n=1, m=1) and Clickable Diols with Azide Groups (M2).

Briefly, 100 mL round bottom flask charged with N-methyldiethanolamine (10 g, 84 mmol) and 30 mL DMF. Slowly dropwise was added propargyl bromide (9.98 g, 84 mmol) under magnetic stirring at room temperature. After 24 h, the reaction was quickly transferred from the round bottom flask to a vial. M1 (n=1, m=1) precipitated from the DMF solution as a sticky material. The supernatant was removed and washed with acetone (since it was only soluble in protic solvents it was not used further). The final product was then put under vacuum for at least 3 days and used without further purification.

2,2-Bis(azidomethyl)propane-1,3-diol (M2) was synthesized as described in Xu et al., *Macromolecules* 2011, 44, 2660-2667. Briefly, 2,2-bis(bromomethyl)propane-1,3-diol (98%, 10.4 g, 40 mmol) was dissolved in DMSO (40 mL) in a 100 mL 3-neck flask equipped with a reflux condenser. Next, sodium azide (6.5 g, 100 mmol) was added under nitrogen. The suspension was heated to 110° C. and stirred for 20 h. After being cooled to room temperature, 30 mL of water was added and the mixture was transferred to a 500 mL separatory funnel and extracted with 90 mL of ethyl acetate 3 times. The combined organic phase was washed with 50 mL of saturated brine 3 times and dried with sodium sulfate. The final product (yellow liquid) was then put under vacuum for at least 3 days before use.

Example 2

Example of Synthesis of Non-Clickable Polyurethane (PU 1), Antimicrobial Polyurethane with Side-Chain Alkyne Groups (PU-Al 1) and Polyurethane with Side-Chain Azide Groups (PU-$N_3$).

Non-clickable polyurethane (PU 1), antimicrobial polyurethane with side-chain alkyne groups (PU-Al 1) and polyurethane with side-chain azide groups (PU-$N_3$ 1) were prepared from the following materials of Table 1:

TABLE 1

| | PU 1 | | PU-Al 1 | | PU-$N_3$ 1 | |
|---|---|---|---|---|---|---|
| | Amount/g | Weight-% | Amount/g | Weight-% | Amount/g | Weight-% |
| Isophoronediisocyanate | 30.00 | 45.20 | 30.00 | 44.18 | 30.00 | 44.16 |
| Polypropylene glycol(Mn = 1000) | 27.50 | 41.43 | 27.50 | 40.13 | 27.50 | 40.48 |
| 1,4-Butanediol | 5.87 | 8.84 | 4.91 | 7.23 | 4.68 | 6.89 |
| N,N-bis(2-hydroxyethyl)-N-methylprop-2-yn-1-aminium (M1, n = 1, m = 1) | 0 | 0 | 2.5 | 3.68 | 0 | 0 |
| 2,2-Bis(azidomethyl)propane-1,3-diol (M2) | 0 | 0 | 0 | 0 | 2.75 | 4.05 |
| Trimethylolpropane | 3.00 | 4.52 | 3 | 4.42 | 3 | 4.42 |
| Total polymer | 66.37 | 100 | 67.91 | 100 | 67.93 | 100 |
| DMF | 132.25 | — | 132.25 | — | 132.25 | — |
| Solid content, % | 33.42% | | 33.93% | | 33.93% | |

The polyurethane samples were prepared according to the above amounts and the following procedure. Firstly, isophoronediisocyanate and polypropylene glycol were charged into a 250 mL dried four-necked flask with a mechanical stirrer, thermometer, condenser, and nitrogen in/outlet. The mixture was uniform after being stirred for 10 min. The temperature of the mixture was increased to 85° C., and the reaction was maintained for 2 h. Then, DMF, 1,4-Butanediol and Trimethylolpropane (for PU1) or 1,4-Butanediol, N,N-bis(2-hydroxyethyl)-N-methylprop-2-yn-1-aminium (M1, n=1, m=1) and Trimethylolpropane (for PU-Al 1) or 1,4-Butanediol, 2,2-Bis(azidomethyl) propane-1,3-diol and Trimethylolpropane (for PU-$N_3$ 1) were added into the flask. The reaction was then maintained for 6-7 h. PU1, PU-Al 1 or PU-$N_3$ 1 were prepared.

Example 3

Example of Synthesis of Non-Clickable Waterborne Polyurethane (WPU 2), Waterborne Polyurethane with Side-Chain Alkyne Groups (WPU-Alkyne 2) and Waterborne Polyurethane with Side-Chain Azide Groups (WPU-Azide 2).

Non-clickable waterborne polyurethane (WPU 2), waterborne polyurethane with side-chain alkyne groups (WPU-alkyne 2), and waterborne polyurethane with side-chain azide groups (WPU-azide 2) were prepared from the following materials of Table 2:

TABLE 2

| | PU 2 | | PU-Al 2 | | PU-N₃ 2 | |
|---|---|---|---|---|---|---|
| | Amount/g | Weight-% | Amount/g | Weight-% | Amount/g | Weight-% |
| 1,6-hexamethylene diisocyanate | 30.00 | 31.96 | 30.00 | 29.99 | 30.00 | 30.92 |
| Polypropylene glycol(Mn = 2000) | 55.00 | 58.60 | 55.00 | 54.97 | 55.00 | 56.68 |
| 1,4-Butanediol | 5.87 | 6.25 | 2.05 | 2.05 | 3.43 | 3.53 |
| N,N-bis(2-hydroxyethyl)-N-methylprop-2-yn-1-aminium (M1, n = 1, m = 1) | 0 | | 10 | | 0 | |
| 2,2-Bis(azidomethyl)propane-1,3-diol (M2) | 0 | | 0 | | 5.6 | 5.77 |
| Trimethylolpropane | 3.00 | 3.20 | 3 | 3.00 | 3 | 3.09 |
| Total polymer | 93.87 | 100 | 100.05 | 100 | 97.03 | 100 |
| DMF | 145.00 | — | 145.00 | — | 145.00 | — |
| Solid content, % | 39.30% | | 40.83% | | 40.08% | |

The polyurethane samples were prepared according to the above amounts and the following procedure. Firstly, 1,6-hexamethylene diisocyanate and polytetramethylene ether glycol were charged into a 500 mL dried four-necked flask with a mechanical stirrer, thermometer, condenser, and nitrogen in/outlet. The mixture was uniform after being stirred for 10 min, and increased the temperature to 85° C., maintained reaction for 2 h. Then, DMF, 1,4-Butanedioland Trimethylolpropane (for PU2) or 1,4-Butanediol, N,N-bis(2-hydroxyethyl)-N-methylprop-2-yn-1-aminium (M1, n=1, m=1) and Trimethylolpropane (for PU-Al 2) or 1,4-Butanediol, 2,2-Bis(azidomethyl) propane-1,3-diol and Trimethylolpropane (for PU-N₃ 2) were added into the flask and kept reaction for 6-7 h. PU1, PU-Al 1 or PU-N₃ 1 were prepared.

Example 4

Example of Synthesis of Clickable Fluorine Containing Molecules with Azide Groups (FG-1)

Clickable fluorine containing molecules with azide groups (FG-1) were synthesized according to Huang et. al., *Journal of Applied Polymer Science*, 2011, 122, 1251-1257. Briefly, A solution of dimethylaminoethyl chloride hydrochloride (20.0 g, 139 mmol) in DMF/water (v/v: 7:3, 150 mL) was added sodium azide (10.0 g, 154 mmol) and a catalytic amount of NaI, followed by heating the mixture at 80° C. for 36 hours. After cooling to room temperature, the mixture was neutralized with solid $Na_2CO_3$. Then NaOH was added to the above solution until pH at around 11. The mixture solution was extracted with ethyl acetate (100 mL) and diethylether (3×60 mL). The combined organic phase was dried with $MgSO_4$, filtered, and the solvent was partially evaporated, slowly and carefully, under vacuum at room temperature. The residual ethylacetate solution was added 1-Iodo-1H,1H,2H,2H-perfluorodecane (100.0 g, 174 mmol) directly. The reaction was heated overnight at 75° C. The obtained yellow solid was collected, washed with EtOAc and diethyl ether yield. The final product (yellow liquid) was then put under vacuum for at least 2 days before use.

Example 5

Example of the Synthesis of Click-Functionalized Molecules: BIT-Al.

To a solution of 1,2-benzisothiazol-3-one BIT (755 mg, 5 mmol) in 10 mL of DMF at 25 degrees C. was added $K_2CO_3$ (1.75 g, 12.5 mmol), and then propargyl bromide (10 mmol) was added. The reaction mixture was stirred at room temperature for 24 h. Upon dilution with water, a light yellow crystalline product was separated and filtered. In another procedure, the mixture was extracted with several portions of chloroform and the volatile material was removed under vacuum. The residue was dissolved in $CH_2Cl_2$ and washed with water. In the two procedures, the combined extracts were dried over anhydrous sodium sulfate. The residue obtained upon evaporation of the solvent was recrystallized from ethanol.

Example 6

Example of the Synthesis of Click-Functionalized Molecules: TMG-Al.

Alkyne-functionalized trimethylguanidine (TMG-Al) was prepared according to the following procedure. 100 mL flask charged with 50 g TMG, and then slowly dropwise added 6.5 g propargyl bromide. The mixture was kept stirred for 16-24 h reaction at room temperature. After completion of the reaction, the solid was filtered and the excess TMG in mother liquor was removed under a pressure-reducing condition. The final product was obtained without further purification.

Example 7

Example of the Synthesis of Click-Functionalized Molecules: TMG-dAl.

Alkyne-functionalized trimethylguanidine (TMG-dAl) was prepared according to the following procedure. A 250-mL flask was charged with 20 g TMG, 50 mL ethanol and then 41 g propargyl bromide was slowly added dropwise. The mixture was kept stirred for 16-24 h reaction at room temperature. After completion of the reaction, the solid was filtered and washed with ethanol. The final product was obtained without further purification.

Example 8

Example of the Synthesis of Click-Functionalized Molecules: PHMG-Al.

Alkyne-functionalized polyhexamethylene guanidine hydrochloride (PHMG-Al) was prepared according to the following procedure. In a 500 mL flask, 25 g PHMG was dissolved in 100 mL DMSO, and heated to 50° C., and then added 0.8 g of sodium ethoxide and 10 g propargyl bromide. The mixture was kept stirred for 16-24 h reaction. After completion of the reaction, water (250 mL) was added and mixed, the aqueous layer was then separated and excess 3-bromo-propynyl extracted with dichloromethane. Removed the solvent and obtained the final product PHMG-Al.

Example 9

Example of the Synthesis of Antimicrobial Polymers Such as Polyurethane with Side-Chain Fluorine and Quaternary Ammonium Containing Molecules (PU-F).

PU-F was prepared according to the following procedure. The click reaction was performed between PU-Al 1 (prepared in Example 2) and FG-1 (prepared in Example 4) as follows: 15 mL water/DMF mixture ($V_{DMF}:V_{H2O}=9:1$), 0.8 g FG-1 were added to 15 g solution of PU-Al 1 in DMF at room temperature under stirring followed by the addition of 0.01 g $CuSO_4.5H_2O$ in 1 mL water-DMF mixed solvent and 0.03 g sodium ascorbate in 1 mL water-DMF mixed solvent, respectively, and then the click reaction was initiated. The mixture was stirred for additional 2 min, then 10 g of mixture was poured into a 6 cm diameter Teflon disk to be dried at 75° C. for 24 h.

Example 10

Example of the Synthesis of Antimicrobial Polymers Such as Polyurethane with Side-Chain BIT (PU-BIT).

PU-BIT was prepared according to the following procedure. The click reaction was performed between PU-$N_3$ 1 (prepared in Example 2) and BIT-Al (prepared in Example 5) as follows: 15 mL water/DMF mixture ($V_{DMF}:V_{H2O}=9:1$), 0.45 g BIT-Al were added to 15 g solution of PU-$N_3$ 1 in DMF at room temperature under stirring followed by the addition of 0.01 g $CuSO_4.5H_2O$ in 1 mL water-DMF mixed solvent and 0.03 g sodium ascorbate in 1 mL water-DMF mixed solvent, respectively, and then the click reaction was initiated. The mixture was stirred for additional 2 min, then 10 g of mixture was poured into a 6 cm diameter Teflon disk to be dried at 75° C. for 24 h.

Example 11

Example of the Synthesis of Antimicrobial Polymers Such as Polyurethane with Side-Chain Trimethylguanidine (PU-TMG).

PU-TMG was prepared according to the following procedure. The click reaction was performed between PU-$N_3$ 2 (prepared in Example 3) and TMG-Al (prepared in Example 6) as follows: 15 mL water/DMF mixture ($V_{DMF}:V_{H2O}=9:1$), 0.31 g TMG-Al were added to 15 g solution of PU-$N_3$ 1 in DMF at room temperature under stirring followed by the addition of 0.01 g $CuSO_4.5H_2O$ in 1 mL water-DMF mixed solvent and 0.03 g sodium ascorbate in 1 mL water-DMF mixed solvent, respectively, and then the click reaction was initiated. The mixture was stirred for additional 2 min, then 10 g of mixture was poured into a 6 cm diameter Teflon disk to be dried at 75° C. for 24 h.

Example 12

Example of the Synthesis of Antimicrobial Polymers Such as PU-dTMG.

PU-dTMG was prepared according to the following procedure. The click reaction was performed between PU-$N_3$ 2 (prepared in Example 3) and TMG-dAl (prepared in Example 7) as follows: 15 mL water/DMF mixture ($V_{DMF}:V_{H2O}=9:1$), 0.25 g TMG-dAl were added to 15 g solution of PU-$N_3$ 1 in DMF at room temperature under stirring followed by the addition of 0.01 g $CuSO_4.5H_2O$ in 1 mL water-DMF mixed solvent and 0.03 g sodium ascorbate in 1 mL water-DMF mixed solvent, respectively, and then the click reaction was initiated. The mixture was stirred for additional 2 min, then 10 g of mixture was poured into a 6 cm diameter Teflon disk to be dried at 75° C. for 24 h.

Example 13

Example of the Synthesis of Antimicrobial Polymers Such as Polyurethane with Side-Chain Polyhexamethylene Guanidine (PU-PHMG).

PU-PHMG was prepared according to the following procedure. The click reaction was performed between PU-$N_3$ 2 (prepared in Example 3) and PHMG-Al (prepared in Example 8) as follows: 15 mL water/DMF mixture ($V_{DMF}:V_{H2O}=9:1$), 1 g PHMG-Al were added to 15 g solution of PU-$N_3$ 1 in DMF at room temperature under stirring followed by the addition of 0.01 g $CuSO_4.5H_2O$ in 1 mL water-DMF mixed solvent and 0.03 g sodium ascorbate in 1 mL water-DMF mixed solvent, respectively, and then the click reaction was initiated. The mixture was stirred for additional 2 min, then 10 g of mixture was poured into a 6 cm diameter Teflon disk to be dried at 75° C. for 24 h.

The invention claimed is:

1. A composition comprising:
a polymer or oligomer formed from a reaction product of:
(i) a compound having the structure of Formula (I):

$$\ce{HC#C-CH2-R1}$$ (I)

wherein $R_1$ comprises a first antimicrobial moiety or a first dehydrogenated antimicrobial moiety, and
(ii) one or more second monomers that react with the compound of (i) to form the polymer or oligomer; and
a reaction product of the formed polymer or oligomer with a compound having the structure of Formula (II):

$$N_3-R_2 \quad (II),$$

wherein $R_2$ comprises a second antimicrobial moiety or a second antimicrobial moiety in which a leaving group of the second antimicrobial moiety has been replaced with the azido group of the structure of Formula (II), and wherein the resulting polymer or oligomer comprises a quaternary ammonium moiety within the backbone and is antimicrobial.

2. The compound of claim 1, wherein $R_1$ comprises tetramethylguanidine (TMG) or dehydrogenated TMG.

3. The compound of claim 1, wherein $R_1$ is joined to the HC≡C—($CH_2$)— moiety of the structure of Formula (I) through a nitrogen-carbon bond.

4. The compound of claim 1, wherein the compound having the structure of Formula (I) comprises Compound (I-1) or Compound (I-2):

(I-1)

and

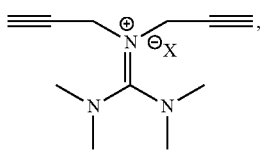

(I-2)

wherein X⁻ is a monovalent anion.

5. The compound of claim 1, wherein $R_2$ comprises a fluorinated hydrocarbon moiety and/or a quaternary ammonium moiety.

6. The compound of claim 5, wherein the fluorinated hydrocarbon moiety is joined to the $N_3$— moiety of the structure of Formula (II) through the quaternary ammonium moiety.

7. The compound of claim 6, wherein the compound having the structure of Formula (II) has the structure of Formula (II-1):

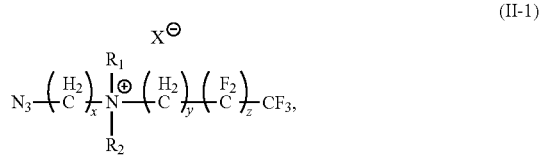

(II-1)

wherein $R_1$ and $R_2$ are each independently a linear or branched C1-C20 alkyl, alkenyl, aryl, or heteroaryl group,
wherein X⁻ is a monovalent anion, and
wherein x, y, and z are each independently an integer from 1 to 20.

8. The compound of claim 1, wherein the polymer or oligomer has a structure of Formula (III):

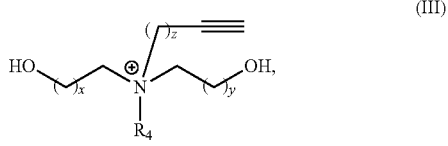

(III)

wherein $R_4$ is a linear or branched C1-C20 alkyl, alkenyl, aryl, or heteroaryl group; and x, y, and z are each independently an integer from 1 to 20.

9. The composition of claim 1, wherein the first antimicrobial moiety or the first dehydrogenated antimicrobial moiety comprises two or more alkyne groups.

10. The composition of claim 1, wherein the polymer or oligomer forms an antimicrobial coating on a surface.

11. The composition of claim 1, wherein the second antimicrobial moiety or the second dehydrogenated antimicrobial moiety comprises two or more azide groups.

12. A method of reducing microbial proliferation on a surface, the method comprising:
disposing the composition of claim 1 on the surface.

13. A method of making an antimicrobial composition comprising:
reacting a compound having the structure of Formula (I):

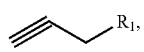

(I)

wherein $R_1$ comprises an antimicrobial moiety or a dehydrogenated antimicrobial moiety, with one or more second monomers that react with the compound of (i) to form a polymer or oligomer, and
reacting the formed polymer or oligomer with a compound having the structure of Formula (II):

$N_3$—$R_2$ (II), wherein $R_2$ comprises an antimicrobial moiety or an antimicrobial moiety in which a leaving group of the second antimicrobial moiety has been replaced with the azido group of the structure of Formula (II), and wherein the resulting polymer or oligomer comprises a quaternary ammonium moiety within the backbone and is antimicrobial.

14. The method of claim 13, wherein the first antimicrobial moiety or the first dehydrogenated antimicrobial moiety comprises two or more alkyne groups.

15. The method of claim 13, wherein the polymer or oligomer comprises a quaternary ammonium moiety within a backbone of the polymer or oligomer, and wherein the polymer or oligomer is antimicrobial.

16. The method of claim 13, wherein the polymer or oligomer forms an antimicrobial coating on a surface.

17. The method of claim 13, wherein the second antimicrobial moiety or the second dehydrogenated antimicrobial moiety comprises two or more azide groups.

18. The method of claim 13, wherein the compound having the structure of Formula (I) comprises Compound (I-1) or Compound (I-2):

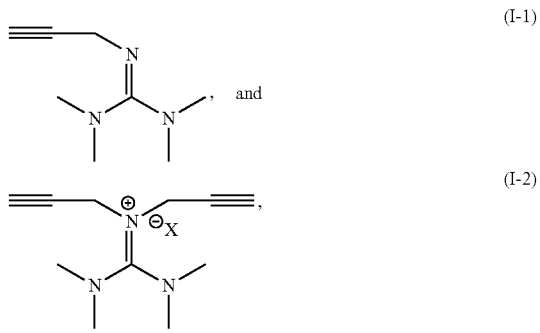

wherein X⁻ is a monovalent anion.

* * * * *